United States Patent [19]

Lin et al.

[11] Patent Number: 5,631,239

[45] Date of Patent: May 20, 1997

[54] L-2',3'-DIDEOXY NUCLEOSIDE ANALOGS AS ANTI-HEPATITIS B (HBV) AGENTS

[75] Inventors: Tai-Shun Lin, North Haven; Yung-Chi Cheng, Woodbridge, both of Conn.

[73] Assignee: Yale University, New Haven, Conn.

[21] Appl. No.: 544,650

[22] Filed: Oct. 18, 1995

Related U.S. Application Data

[63] Continuation of Ser. No. 67,299, May 25, 1993, abandoned.
[51] Int. Cl.$^6$ ................................................ A61K 31/70
[52] U.S. Cl. ........................ 514/49; 514/50; 514/893; 514/894; 536/28.2; 536/28.52
[58] Field of Search ........................... 536/28.2, 28.52; 514/50, 893, 894

[56] References Cited

U.S. PATENT DOCUMENTS 4,788,181  11/1988  Driscoll et al. .

FOREIGN PATENT DOCUMENTS

| 0409227 | 1/1991 | European Pat. Off. . |
| 0587364 | 3/1994 | European Pat. Off. . |
| 4224737 | 2/1994 | Germany . |
| 1100191 | 4/1989 | Japan . |
| 1143892 | 6/1989 | Japan . |
| 9001036 | 2/1990 | WIPO . |
| 9214743 | 9/1992 | WIPO . |
| 9220696 | 11/1992 | WIPO . |
| 9409793 | 5/1994 | WIPO . |
| 9414456 | 7/1994 | WIPO . |
| 9507086 | 3/1995 | WIPO . |

OTHER PUBLICATIONS

Du et al. "Comparison of the In Vitro Toxicity . . . " Int. J. Cell Clon. 10:87 (1992)
Siddiqui et al. "Chemistry and Anti-HIV Properties . . . " J. Med. Chem. 35:2195 (1992).
Okabe et al. "Synthesis of F-ddC" J. Org. Chem. 56:4392 (1991).
Doong, et al. "Inhibition of the Replication of Hepatitis B . . . " Proc. Natl. Acad. Sci USA, vol. 88, pp. 8495–8499, Oct. 199.
Huang, et al. "A Facile Synthesis of 4'-Thio-2'-Deoxypyrimid" Nucleosides & Nucleotides, 12(2), pp. 139–147, 1993.
Mansuri, et al. "Preparation of the Geometric Isomers . . . " Bioorganic & Medicinal Chemistry Letters, vol. 1, No. 1, pp. 65–68, 1.
Fujimori, et al. "A Convenient and StereoSelective Synthesis . . . " Nucleosides & Nucleotides, 11(2–4), pp. 341–349, 1992.
Secrist, et al., "Synthesis and Anti–HIV Activity of 4'–Thio . . . " Journal Medical Chemistry, vol. 35, pp. 533–538, 1992.
Secrist, et al., "Synthesis and Biological Activity of 2'–Deoxy . . . " Journal Medical Chemistry, vol. 34, pp. 2361–2366, 1991.
Ravid, et al, "Synthesis of the Enantiomers of 4–Substituted Tetrahedron", vol. 34, pp. 1453–1455, 1978.

Hanessian, et al. "Stereochemical Control of Nature's . . . " Tetrahedron, vol. 43, No. 21, pp. 5055–5072, 1987.
Spadari, et al., "L–Thymidine is Phosphorylated by Herpes . . . " Journal Medical Chemistry, vol. 35, pp. 4214–4220, 1992.
Barton, et al. "The Invention of Radical Reactions. Part XXIX . . . " Tetrahedron, vol. 49, No. 14, pp. 2793–2804, 1993.
Taniguchi, et al., "Stereochemical Studies—XXX'. . . " Tetrahedron, vol. 30, pp. 3547 to 3552, 1974.
Lin, et al., "Antiviral Activity of 2',3'–Dideoxyctidin–2' . . . " Biochemical Pharmacology, vol. 36, No. 3, pp. 311–316, 1987.
Horwitz, et al., "Nucleosides. XI. 2',3'–Dideoxycytidine" Journal of Organic Chemistry, vol. 32, pp. 817–818, Mar. 1967.
Chang, et al. "Biological Pharmacology . . . " in J. of Biological Chemistry. v.267, No. 31. Nov. 5, 1992. pp. 22414–22420.
Yokota, et al. "Comparative Activities . . . " in Antimicrobial Age And Chemotherapy. v.34, No. 7. 1990. pp. 1326–1330.
Chen, Chin–Ho and Yung–Chi Cheng. "Delayed Cytotoxicity and Selective Loss . . . " in J. of Biological Chemistry. v.264, No.20. Jul. 15, 1989. pp. 11934–1193.
Larder, et al. "Susceptibilities of Zidovudine–Susceptible . . . " in Antimicrol Agents and Chemotherapy, v.34, No.3. Mar. 1990. pp. 436–441.
DiBisceglie, et al. "Hepatocellular Carcinoma" in Annals of Internal Medicine. 1988; 108: 390–401.
World Health Organization. "Progress in the Control of Viral Hepatitis . . . " in Bulletin of the World Health Organization. 66(4):443–455 (1988).
Price, et al. "Inhibition of the Replication of Hepatitis B . . . " in Proc. Natl. Acad. Sci. USA, vol. 86, pp. 8541–8544. Nov. 1989.
Suzuki, et al. "Inhibition of Duck Hepatitis B Virus . . . " in Biomedi and Biophysical Research Communications. v.156, No.3, Nov. 15, 1988. pp. 1144–1151.
"Antiviral Treatment of Hepatitis B".
Chang, et al. "Deoxycytidine Deaminase–Resistant Stereoisomer" in J. of Biological Chemistry. v.267, pp. 13938–13942, 1992.
Kim et al. "Potential Anti–AIDS Drugs" J. Med. Chem 30:862 (1987).

Primary Examiner—James O. Wilson
Attorney, Agent, or Firm—Henry D. Coleman; R. Neil Sudol

[57] ABSTRACT

The present invention relates to the surprising discovery that certain dideoxynucleoside analogs which contain a dideoxy ribofuranosyl moiety having an L-configuration (as opposed to the naturally occurring D- configuration) exhibit unexpected activity against Hepatitis B virus (HBV). In particular, the compounds according to the present invention show potent inhibition of the replication of the virus in combination with very low toxicity to the host cells (i.e., animal or human tissue). Compounds according to the present invention exhibit primary utility as agents for inhibiting the growth or replication of HBV, HIV and other retroviruses, most preferably HBV.

3 Claims, 14 Drawing Sheets

SCHEME 1

SCHEME 1

R = H, F, Cl, Br, I, CH₃, etc.

SCHEME 2

R = H, F, Cl, Br, I, CH₃, etc.

SCHEME 3

SCHEME 4

SCHEME 5

SCHEME 6

R = H, F, Cl, Br, I, CH₃, etc.

SCHEME 7

SCHEME 8

SCHEME 8

R = -Si(*t*-Bu)Ph$_2$

X = H, F, Cl, Br, I, CH$_3$, etc.

SCHEME 9

R = -Si(t-Bu)Ph$_2$

X = CH$_3$, Et, F, Cl, Br, I,

C≡CH, HC=CH$_2$,

SCHEME 10

SCHEME 11

L-2',3'-DIDEOXY NUCLEOSIDE ANALOGS AS ANTI-HEPATITIS B (HBV) AGENTS

This work is supported by National Institutes of Health Grants CA44358 and AI29430. The United States Government retains certain rights in the invention.

This is a continuation of application Ser. No. 08/067,299 filed May 25, 1993, now abandoned.

FIELD OF THE INVENTION

This invention relates to dideoxy nucleoside analogs. These compounds exhibit significant activity against retroviruses, and in particular, Hepatitis B virus. This invention also relates to pharmaceutical compositions containing these compounds and to methods of inhibiting the growth or replication of Hepatitis B virus as well as treating Hepatitis B viral infections in animals and in particular, humans.

BACKGROUND OF THE INVENTION

Hepatitis B virus (HBV) infection is a major health problem throughout the world. HBV is a causative agent of both an acute and chronic form of hepatitis. It is estimated that more than 200 million people worldwide are chronic carriers of HBV.

HBV belongs to the family Hepadnaviridae, which includes a number of related viruses which primarily infect small rodents. All members of the hepadnavirus family have a number of characteristics in common such as morphological appearance, antigenic makeup and DNA size and structure. Pathological findings following infection with the members of this family are quite similar. Studies show that the replication and spread of the viruses of this family are dependent upon the reverse transcriptase of an RNA intermediate.

HBV itself is a double-stranded DNA virus. Its DNA polymerase catalyzes both DNA-dependent and RNA-dependent DNA synthesis. There is presently no effective drug for the treatment of an HBV infection.

The best defense against Hepatitis B viral infection is vaccination. However, even with the advent of immunization programs, the disease remains a severe worldwide problem. Although acute Hepatitis B viral infections are generally self-limiting, in many instances the disease can progress to the chronic state. A Hepatitis B viral infection also creates a risk to fulminant hepatitis. In addition, Hepatitis B viral infections are closely associated with hepatocellular carcinoma.

Present therapy for the treatment of chronic Hepatitis B viral infections includes the administration of interferon alpha, and various nucleoside analogs such as adenine arabinoside or its monophosphate (ara-AMP). These therapeutic approaches have met with limited success. The use of AZT, acyclovir and foscarnet (in the case of fulminant hepatitis) to treat hepatitis has also been tried with little, if any, success.

Several 2',3'-dideoxynucleoside analogs have been reported in the literature to exhibit potent activity against Hepatitis B virus in culture. In particular, the nucleoside analogs (+) and (−)-2',3'-Dideoxy-3'-thiacytidine ((±) SddC) have been shown to be potent inhibitors of Hepatitis B virus and the (−)isomer was particularly interesting in that it exhibited relatively low toxicity along with its potent activity. The 5-fluoro analog ((±)5-FSddC) was also shown to exhibit potent activity. (Chang, et al., *Jour. Biol. Chem.*, 267, 222414, 1992 and Chang, et at., *Jour. Biol. Chem.*, 267, 13938, 1992).

A number of 2',3'-dideoxynucleoside analogs have exhibited significant activity against human immunodeficiency virus (HIV), including 3'-deoxy-2',3'-didehydrothymidine (D4T), 2',3'-dideoxy-2',3'-didehydroguanosine (Carbovir), 2',3'-dideoxycytidine (DDC), 3'-azido-2',3'-dideoxyguanosine (AZG), 2',3'-dideoxyinosine (DDI), 2',3'-dideoxy-2',3'-didehydrocytidine, 3'-fluoro-2',3'-dideoxyadenosine, 3'-fluoro-3'-deoxythymidine and 3'-azido-2',3'-dideoxyuridine. See, Larder, et al., *Antimicrob. Agents Chemother.*, 34, 436 (1990). Certain of these analogs, including ddC, are currently used as anti-HIV agents. Among the dideoxynucleosides, ddC has been shown to be among the most potent inhibitors of HIV.

Although research has concentrated on discovering an effective treatment protocol against HBV and certain potent anti-HBV nucleoside analogs have been synthesized and characterized, an ideal drug has not been found primarily because of the adverse effects that the present compounds elicit.

The major problem in optimizing a treatment protocol against HBV is to provide acceptable anti-HBV activity while minimizing the toxicity to the host cell as well as the anti-mitochondrial DNA effects that many present anti-HBV nucleosides exhibit.

The present invention relates to synthetic nucleosides which exhibit potent anti-viral activity (in particular, anti-HBV activity) with significantly reduced toxicity to the host cell. In contrast to the prior art compounds, the analogs of the present invention represent a viable medicinal therapeutic approach to HBV infections.

OBJECTS OF THE INVENTION

It is an object of the present invention to provide novel nucleoside compounds which may be used to inhibit the growth or replication of HBV or other retroviruses, including HIV.

It is another object of the present invention to provide compounds which exhibit significant inhibitory activity against HBV while minimizing toxicity to the host.

It is a further object of the present invention to provide a method for inhibiting the growth or replication of HBV and other retroviruses, including HIV.

It is yet another object of the present invention to provide a therapeutic method for treating retroviral infections, especially including HBV infections.

It is still an additional object of the present invention to provide a therapeutic method for treating patients having a chronic HBV infection.

These and other objects of the present invention may be readily gleaned from a detailed reading of the description of the present invention which follows.

BRIEF DESCRIPTION OF THE INVENTION

The present invention relates to the surprising discovery that certain dideoxynucleoside analogs which contain a dideoxy ribofuranosyl moiety having an L-configuration (as opposed to the naturally occurring D- configuration) exhibit unexpected activity against Hepatitis B virus (HBV). In particular, the compounds according to the present invention show potent inhibition of the replication of the virus in combination with very low toxicity to the host cells (i.e., animal or human tissue). This is an unexpected result.

Compounds according to the present invention exhibit primary utility as agents for inhibiting the growth or replication of HBV, HIV and other retroviruses, most preferably HBV. Certain of these agents also may be useful for inhibiting the growth or replication of other viruses or for treating other viral infections, certain types of fungal infections, microbial infections and/or related disease states. In addition, certain of these agents may be useful as intermediates for producing or synthesizing related chemical species.

Compounds of the present invention find particular use in combating viral infections which afflict animals, and in particular, humans suffering from hepatitis B viral infections. Compounds according to the present invention offer great potential as therapeutic agents against a disease state (chronic HBV infection) for which there presently are few real therapeutic options. The compounds according to the present invention may be used alone or in combination with agents or other therapeutic treatments.

The compounds of the present invention are dideoxynucleoside analogs which contain a dideoxyribofuranosyl moiety having an L-configuration (in contrast to the natural D-configuration of the sugar moiety). Compounds according to the present invention are disclosed which contain natural or synthetic nucleic acid bases including adenine, guanine, cytosine, thymine and uracil and substituted derivatives of these bases. Compounds of the present invention may also contain certain modifications of the ribofuranosyl moiety.

The present invention also relates to methods for inhibiting the growth or replication of HBV comprising exposing the virus to an inhibitory effective amount or concentration of at least one of the disclosed L-2',3'-dideoxynucleoside analogs. This method may be used in comparison tests such as assays for determining the activities of related anti-HBV compounds as well for determining the susceptibility of a patient's HBV infection to one of the compounds according to the present invention. The present invention may also be used in treating viral infections.

The therapeutic aspect according to the present invention relates to methods for treating retroviral infections in animal or human patients, in particular, HBV or HIV infections in humans comprising administering anti-viral effective amounts of the compounds according to the present invention to inhibit the growth or replication of the viruses in the animal or human patient being treated.

Pharmaceutical compositions based upon these novel chemical compounds comprise the above-described compounds in a therapeutically effective amount for treating a viral, preferably a Hepatitis B viral infection, optionally in combination with a pharmaceutically acceptable additive, carrier or excipient.

Certain of the compounds, in pharmaceutical dosage form, may be used as prophylactic agents for inhibiting the growth or replication of the viral infection. These may be particularly appropriate as anti-HBV or anti-HIV agents. In certain pharmaceutical dosage forms, the pro-drug form of the compounds according to the present invention are preferred.

While not being limited by way of theory, it is believed that the compounds according to the present invention induce their inhibitory effect on the growth or replication of HBV or HIV by functioning as anti-metabolites of the reverse transcriptase enzyme of HBV.

The compounds according to the present invention are produced by synthetic methods which are readily known to those of ordinary skill in the art and include various chemical synthetic methods.

BRIEF DESCRIPTION OF THE FIGURES

FIG. 1 (Scheme 1) depicts the chemical synthesis of uridine and cytidine nucleoside analogs according to the description of example 1.

FIG. 2 (Scheme 2) depicts an alternative chemical synthesis of cytidine nucleoside analogs according to the description of example 1.

FIG. 3 (Scheme 3) depicts a stereospecific synthesis of a cytidine nucleoside analog (compound 12) according to the description of example 1.

FIG. 4 (Scheme 4) depicts the chemical synthesis of a adenosine and guanosine nucleoside analogs according to the description of example 2.

FIG. 5 (Scheme 5) depicts the chemical synthesis of adenosine nucleoside analogs according to the description of example 3.

FIG. 6 (Scheme 6) depicts the chemical synthesis of didehydro cytidine nucleoside analogs according to the description of example 4.

FIG. 7 (Scheme 7) depicts the chemical synthesis of adenosine nucleoside analogs according to the description of example 5.

FIG. 8 (Scheme 8) depicts the chemical synthesis of cytidine nucleoside analogs according to the description of example 6.

FIG. 9 (Scheme 9) depicts the chemical synthesis of uridine nucleoside analogs according to the description of example 7.

FIG. 10 (Scheme 10) depicts the chemical synthesis of adenosine and guanosine nucleoside analogs according to the description of example 8.

FIG. 11 (Scheme 11) depicts the chemical synthesis of adenosine nucleoside analogs according to the description of example 9.

DETAILED DESCRIPTION OF THE PRESENT INVENTION

Figure 1A:
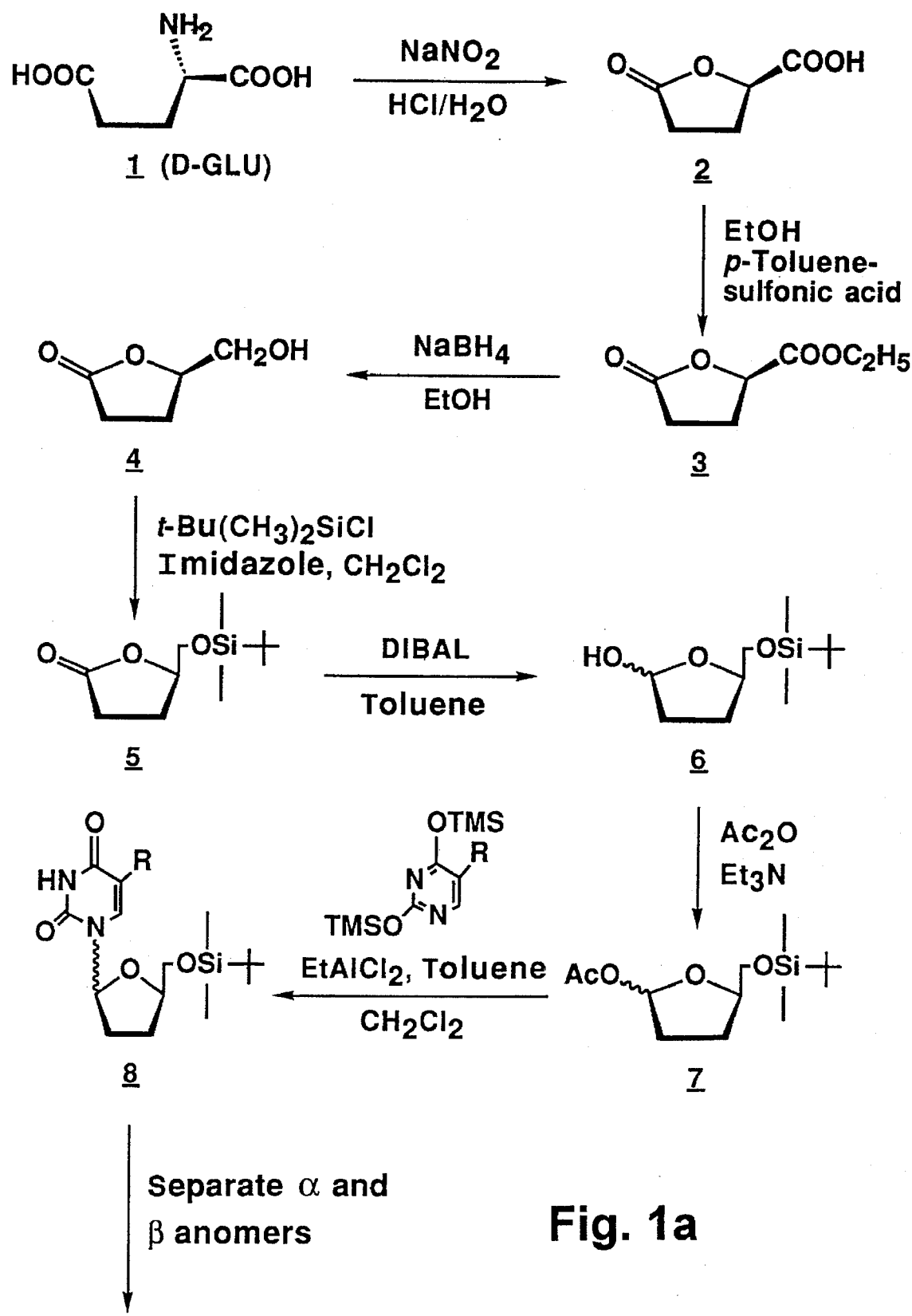
FIGS. 1–11 (Schemes 1–11) depict the synthetic chemical steps which are used to synthesize the compounds according to the present invention. Schemes pertaining to the synthesis of a particular composition are referenced in the examples set forth herein.
Figure 1B:
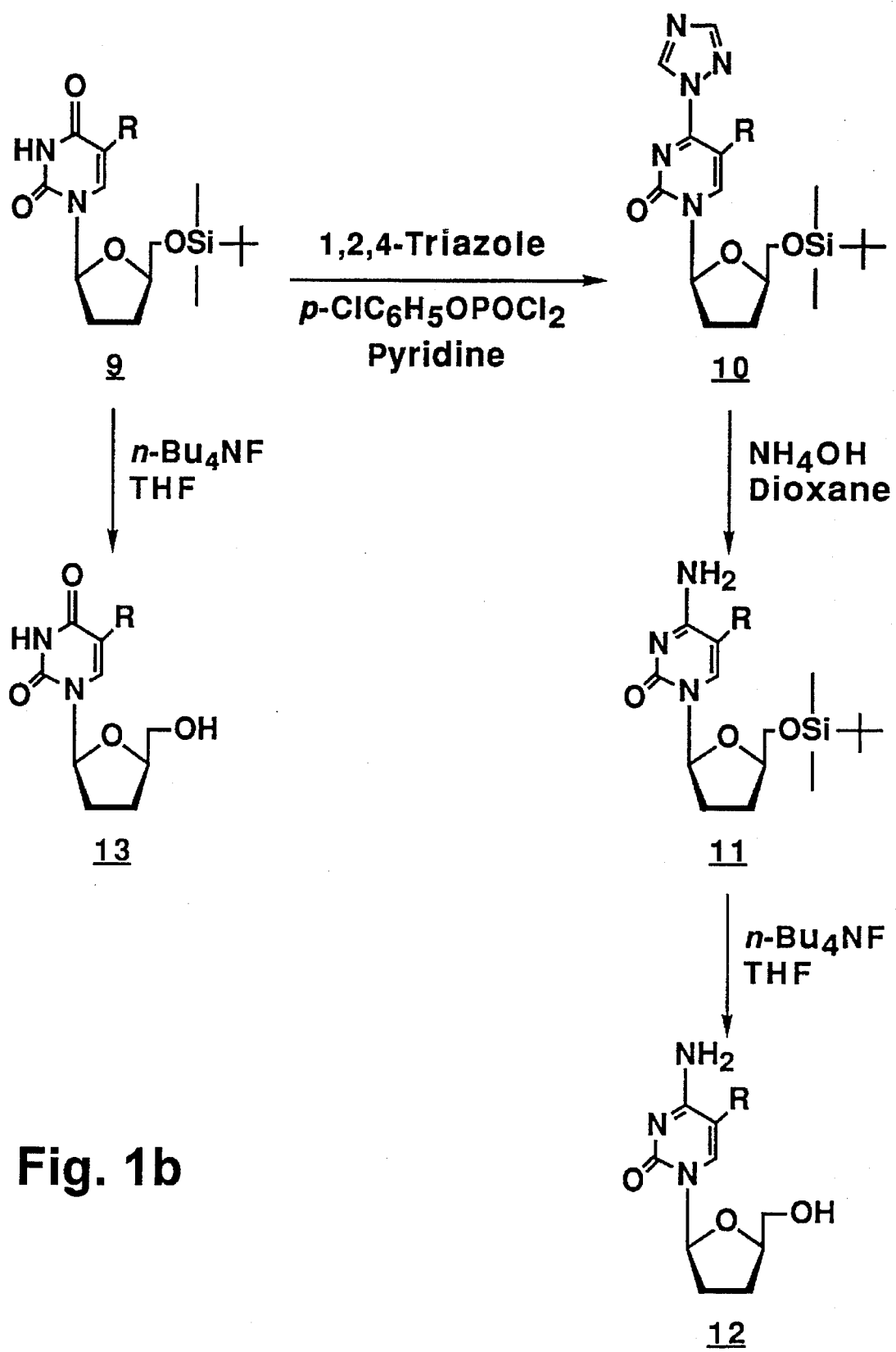
Figure 2:
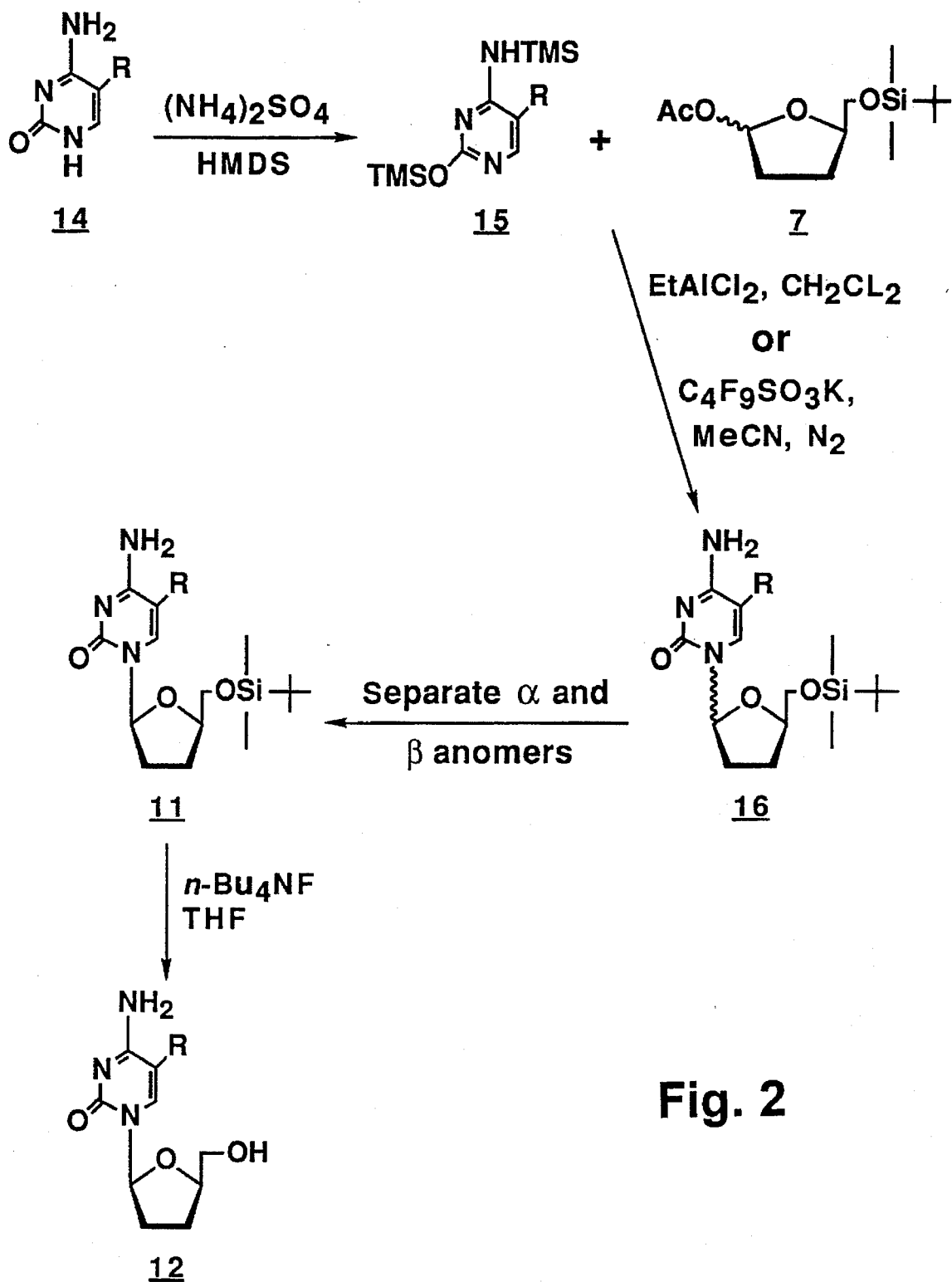
Figure 3A:
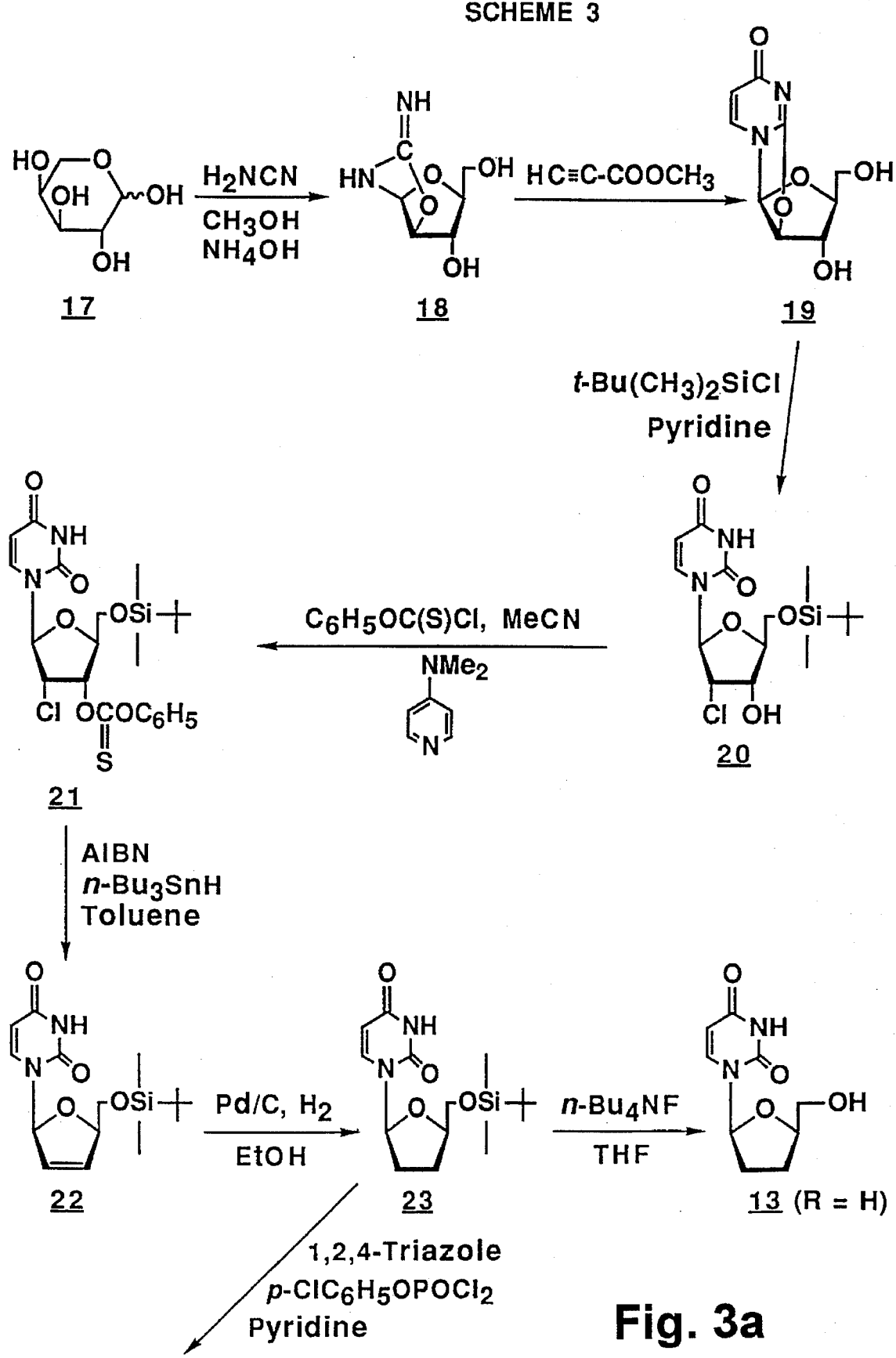
Figure 3B:
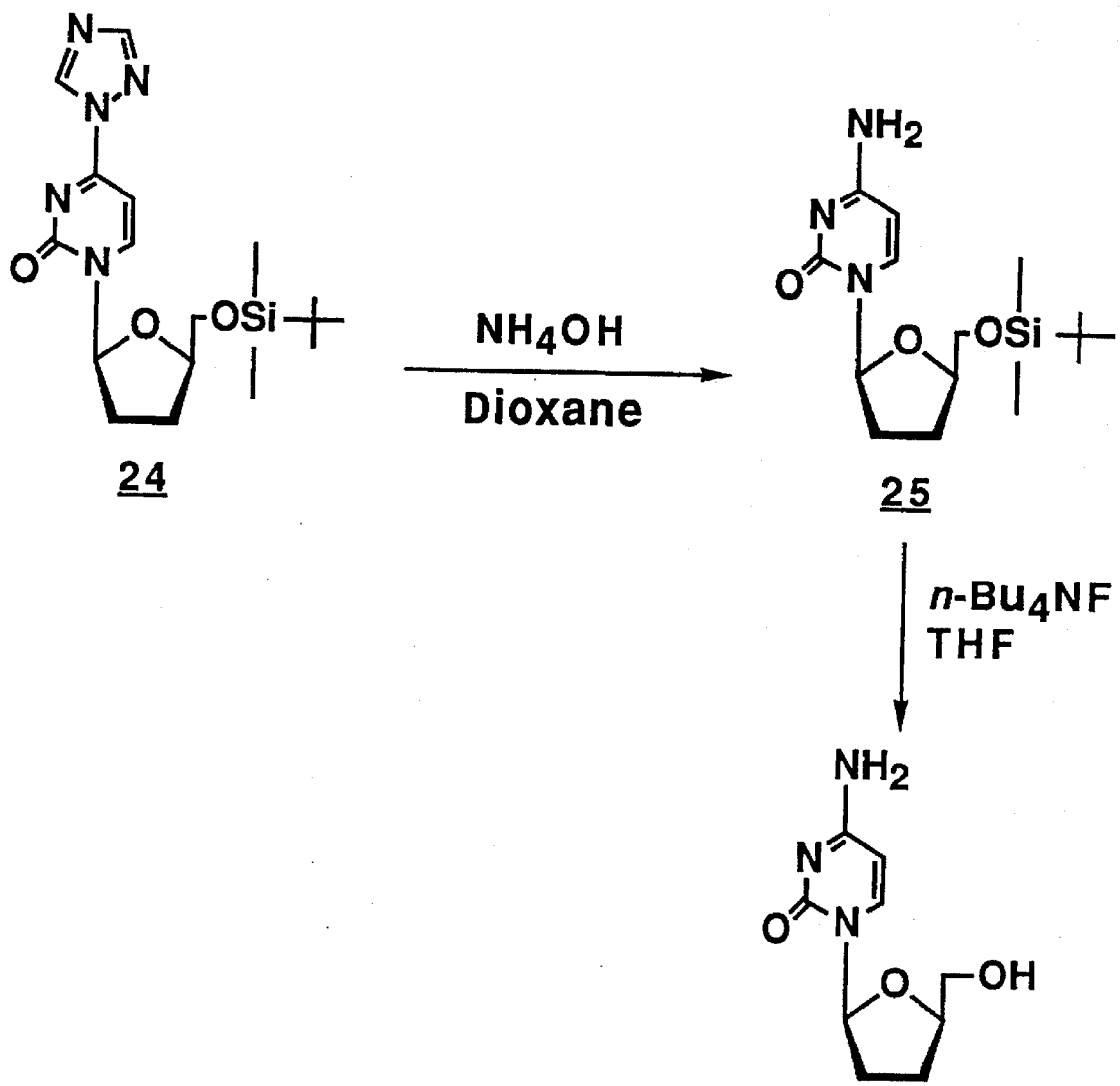
Figure 4:
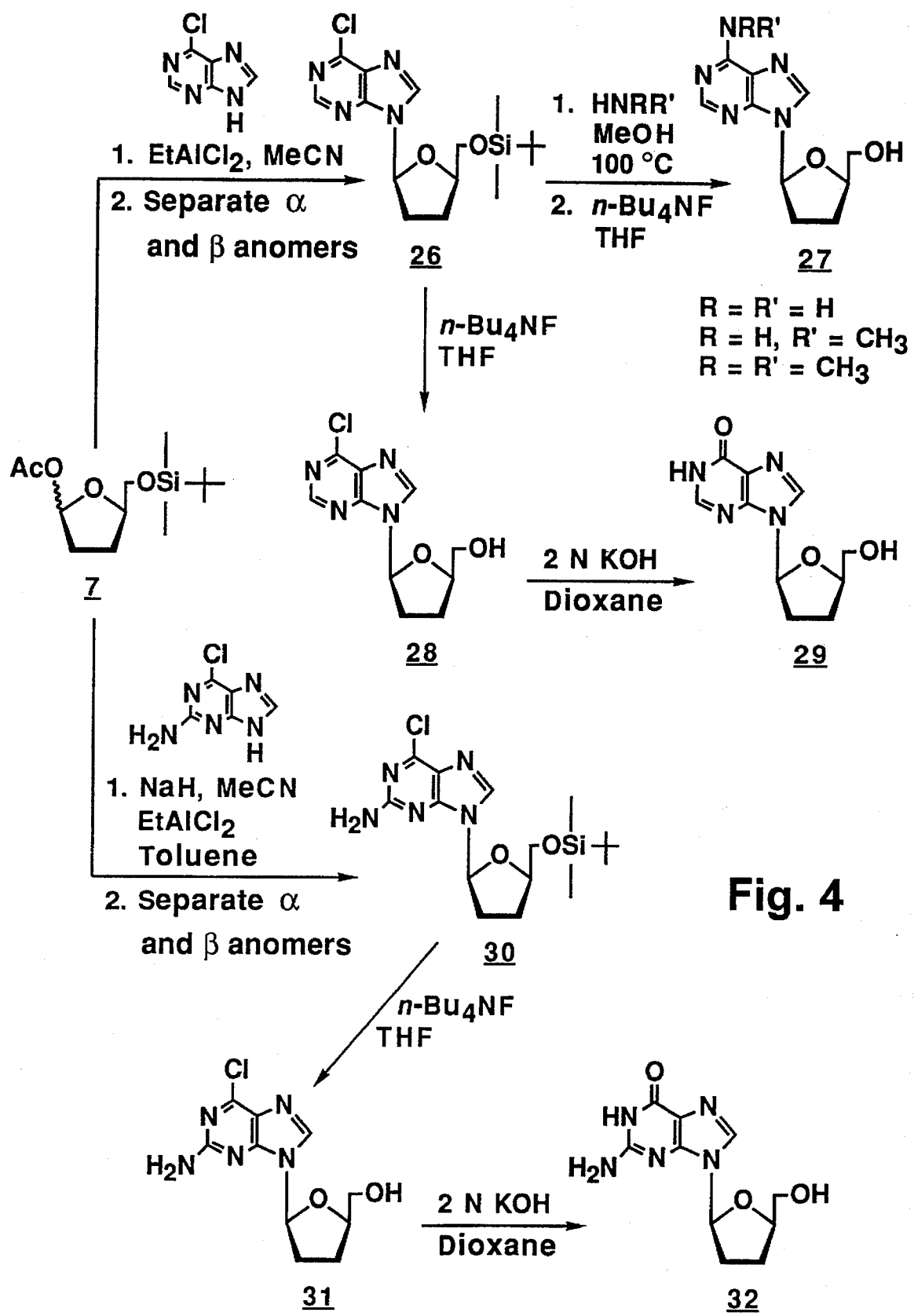
Figure 5:
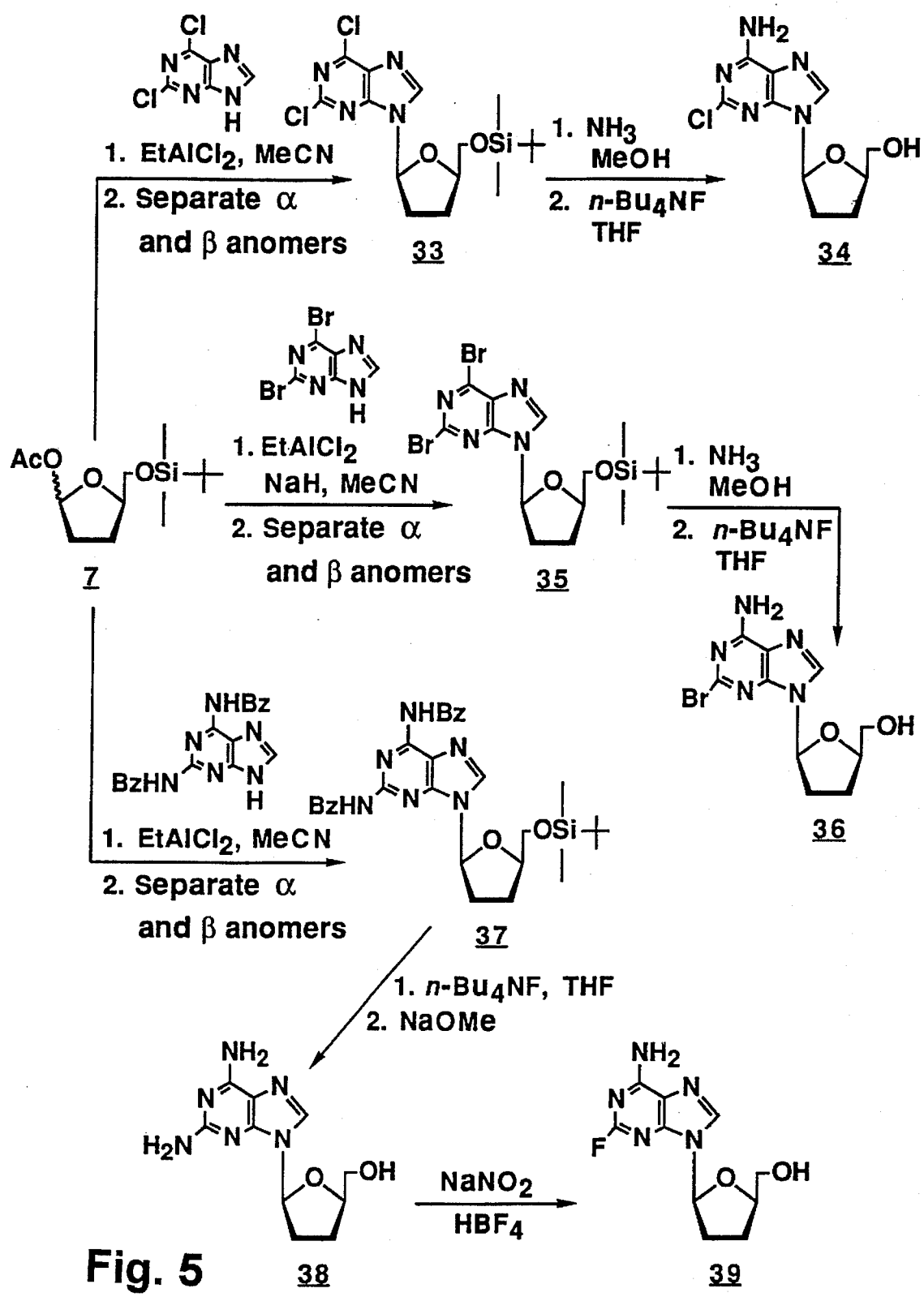
Figure 6:
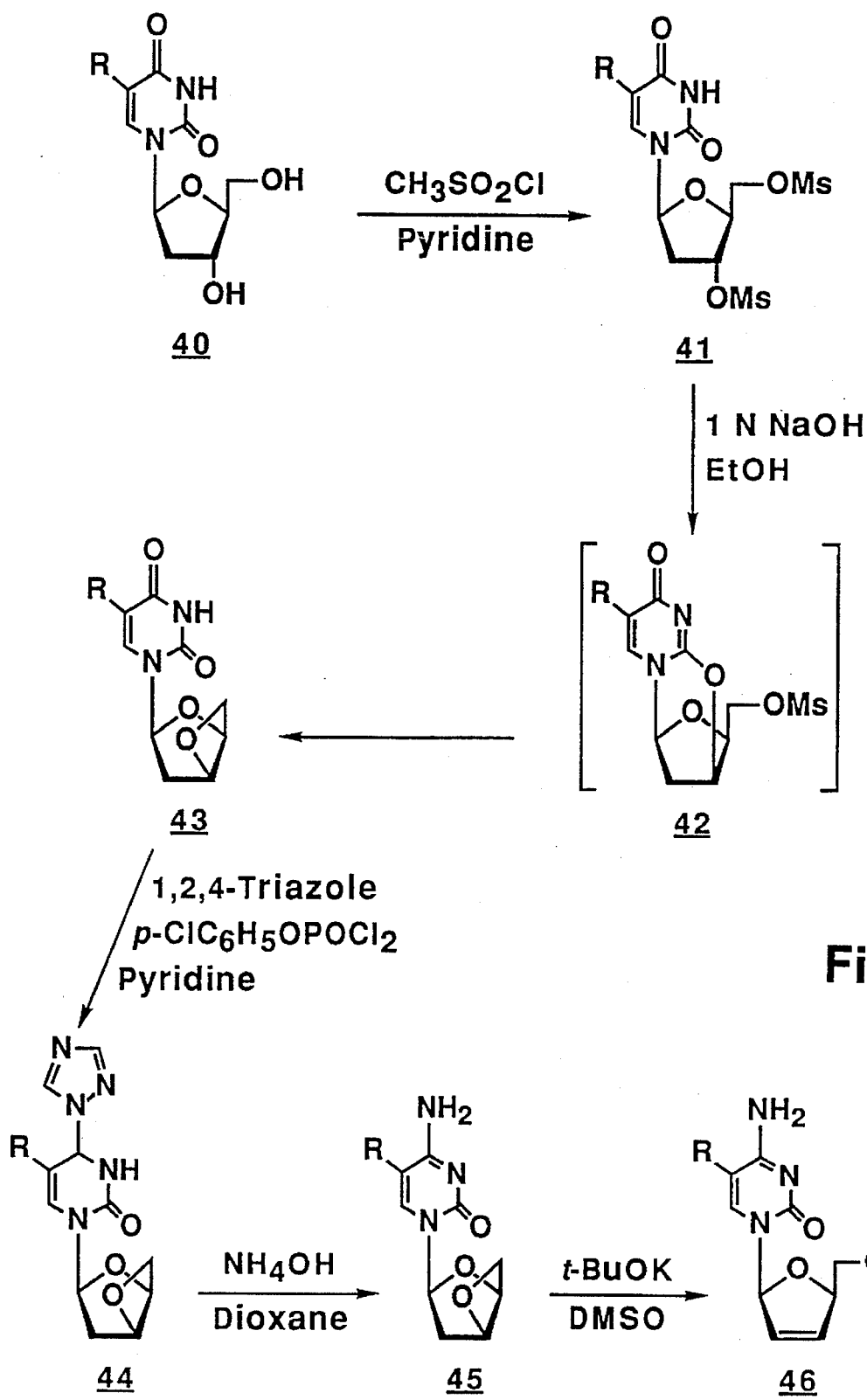
Figure 7:
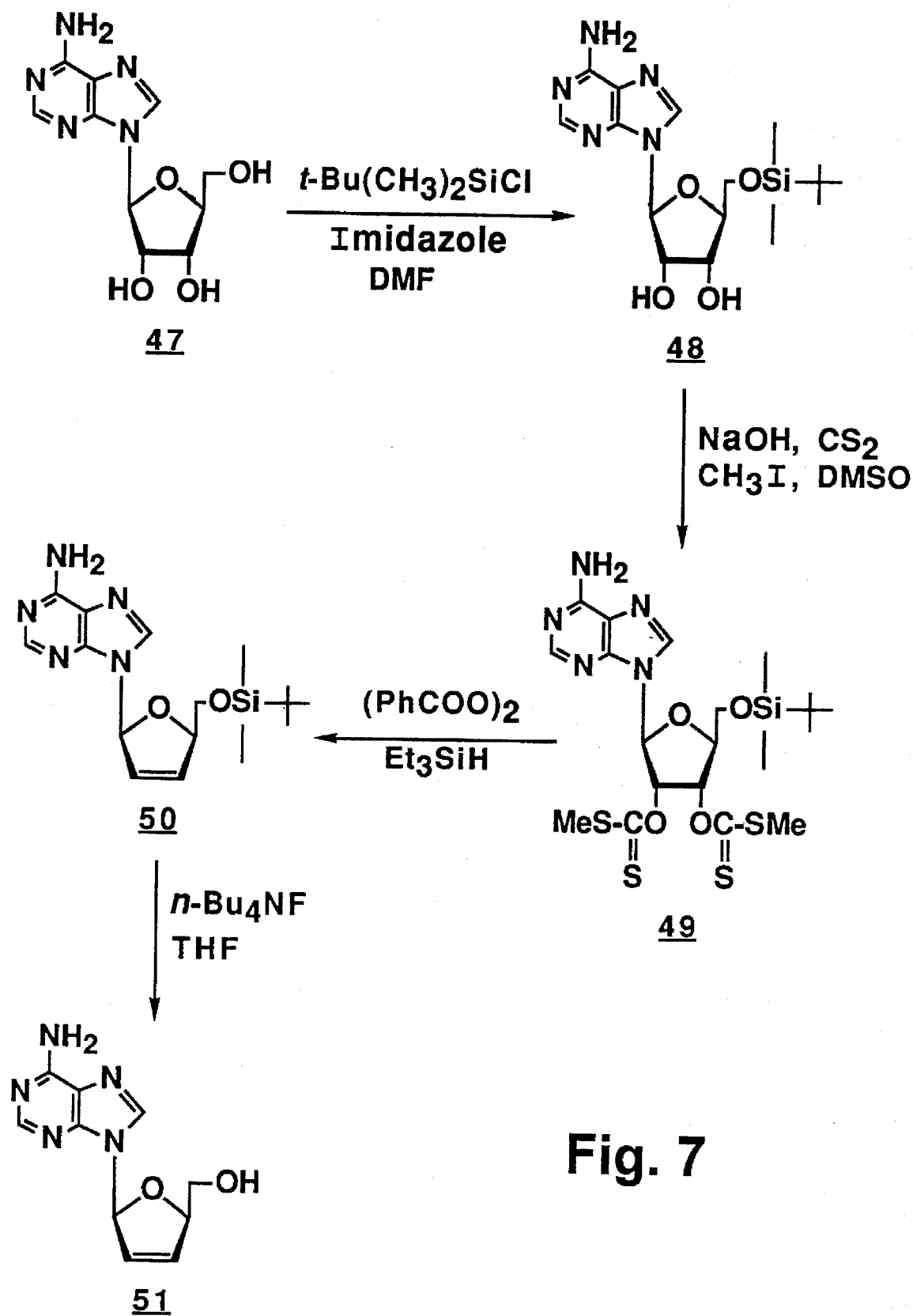
Figure 8A:
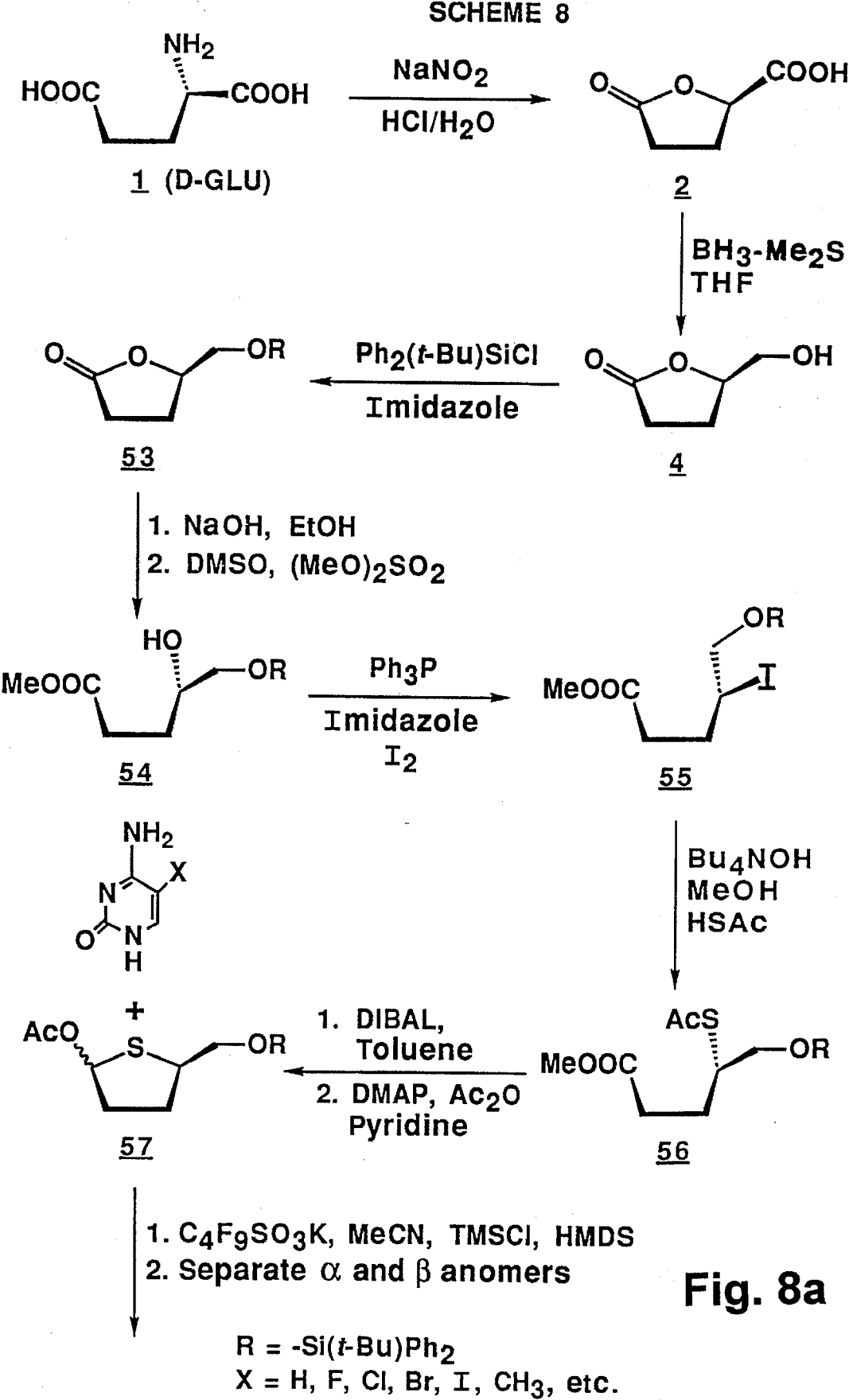
Figure 8B:
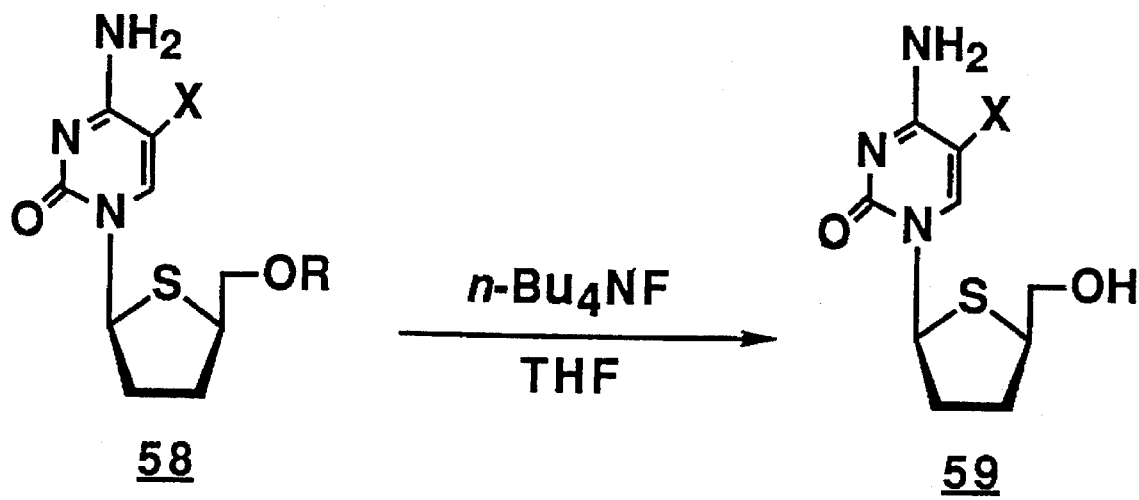
Figure 9:
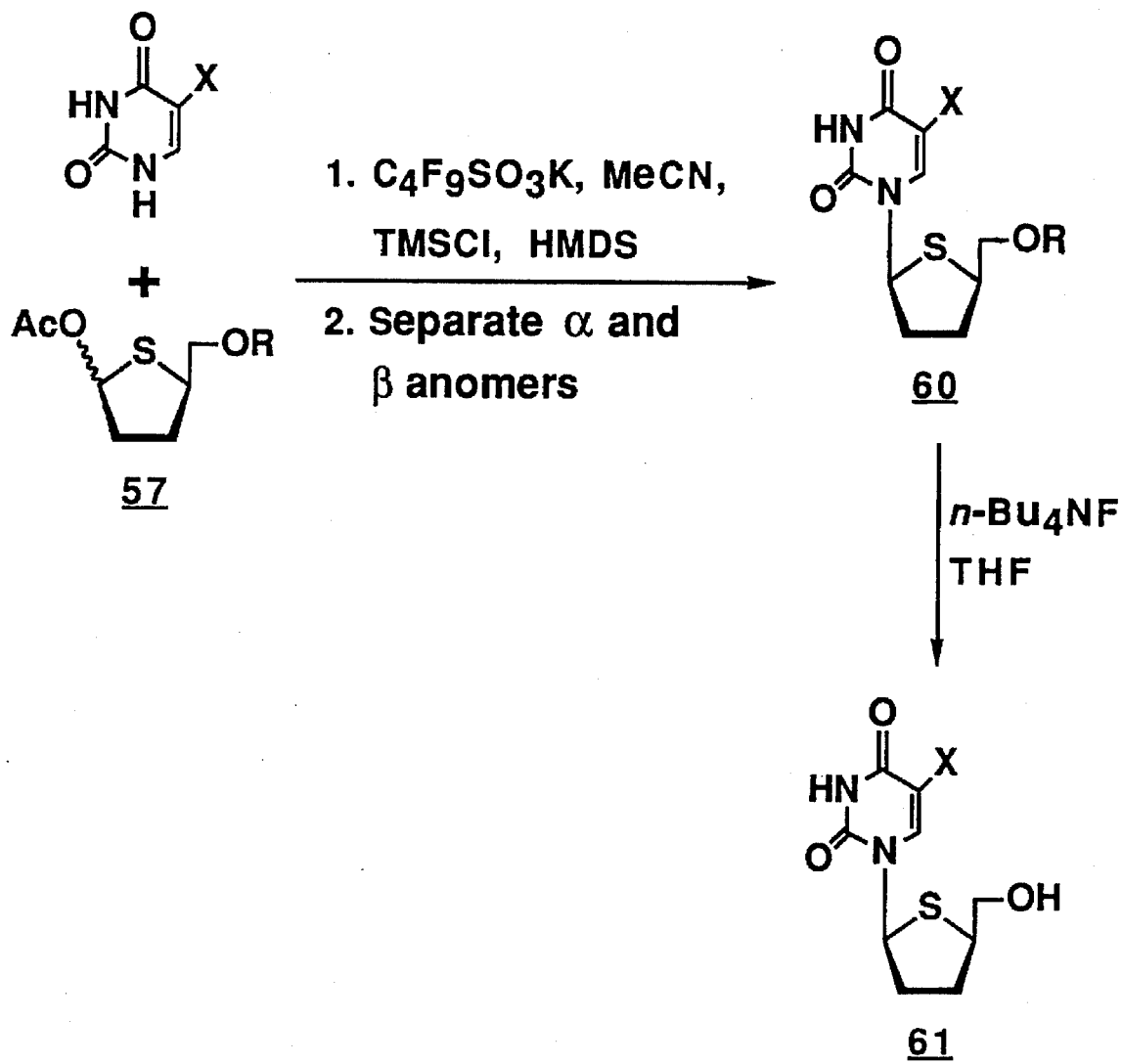
Figure 9:
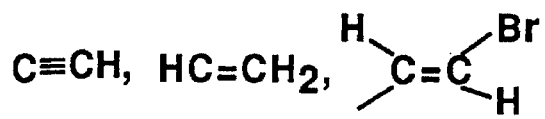
Figure 10:
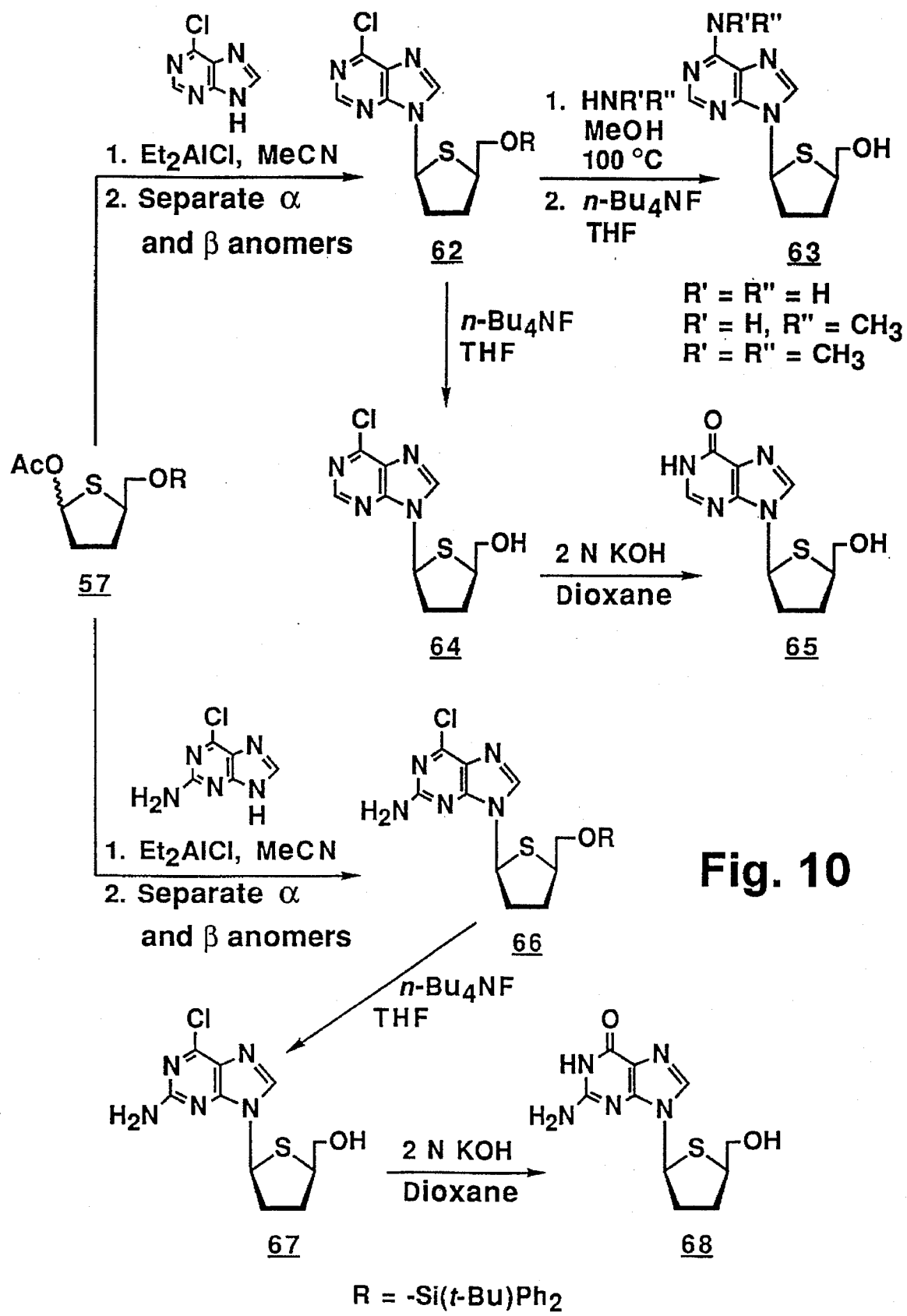
Figure 11:
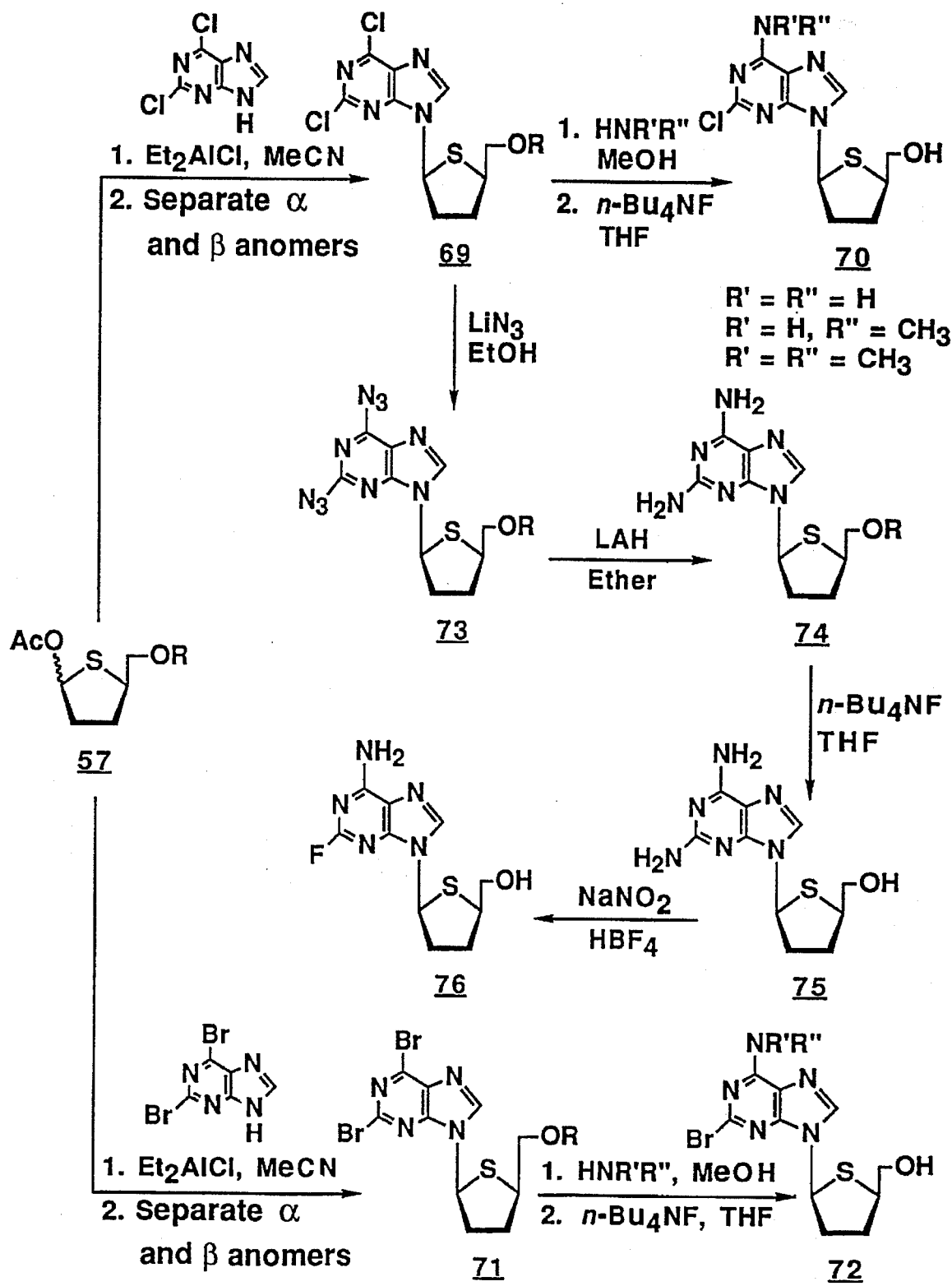

The following definitions will be used throughout the specification to describe the present invention.

The term "dideoxy" is used throughout the specification to describe ribofuranosyl moieties which contain hydrogens rather than hydroxyls at the 2' and 3' positions of the sugar in the present compounds.

The term "didehydro" is used throughout the specification to describe ribofuranosyl moieties which contain a double bond. For example, 2',3'-didehydro refers to a ribofuranosyl moiety containing a double bond between the 2' and 3' carbons of the sugar.

The term "inhibitory effective concentration" or "inhibitory effective amount" is used throughout the specification to describe concentrations or amounts of compounds according to the present invention which substantially or appreciably inhibit the growth or replication of susceptible viruses, especially including HBV or HIV.

The term "therapeutic effective amount" is used throughout the specification to describe concentrations or amounts of compounds according to the present invention which are therapeutically effective in treating retroviral infections, and in particular, HBV infections in humans.

The term "L-configuration" is used throughout the specification to describe the chemical configuration of the dideoxyribofuranosyl moiety of compounds according to the present invention. The L-configuration of the sugar moiety of compounds of the present invention contrasts with the D-configuration of ribose sugar moieties of the naturally occurring nucleosides cytidine, adenosine, thymidine, guanosine and uridine.

The present invention relates to the surprising discovery that certain dideoxynucleoside analogs which contain a dideoxy ribofuranosyl moiety having an L-configuration (as opposed to the naturally occurring D- configuration) exhibit unexpected activity against Hepatitis B virus (HBV). In particular, the compounds according to the present invention show potent inhibition of the replication of the virus in combination with very low toxicity to the host cells (i.e., animal or human tissue).

The present invention relates to a first group of compounds according to the structure:

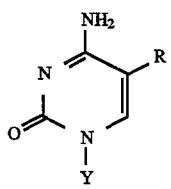

where Y is

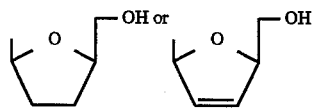

and R is H, F, Cl, Br, I or $CH_3$.

In this first group of compounds, R is preferably H or F.

The present invention also relates to a second group of compounds according to the structure:

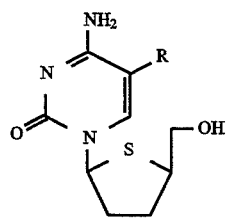

where R is H, F, Cl, Br, I or $CH_3$.

In this second group of compounds, R is preferably H or F, most preferably H.

The present invention also relates to a third group of compounds according to the structure:

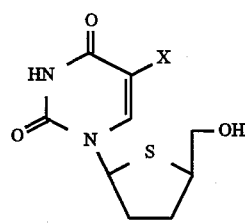

where X is H, F, Cl, Br, I, $CH_3$, —C≡CH, —HC=$CH_2$ or

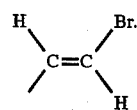

In this third group of compounds, X is preferably H, F or $CH_3$, most preferably $CH_3$.

The present invention also relates to a fourth group of compounds according to the structure:

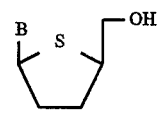

where B is

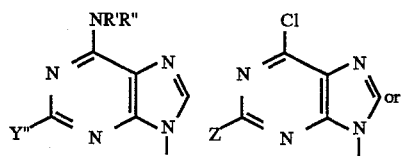

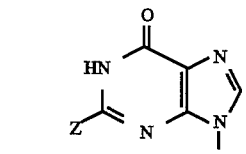

R' is H or $CH_3$;

R" H or $CH_3$;

Y" is H, F, Br, Cl or $NH_2$ when R' and R" are H and

Y" is H when at least one of R' or R" is $CH_3$; and Z is H or $NH_2$.

In this fourth group of compounds according to the present invention, R' and R" are preferably H and Y" is preferably H. Z is preferably $NH_2$.

The present invention also relates to compounds having the structures:

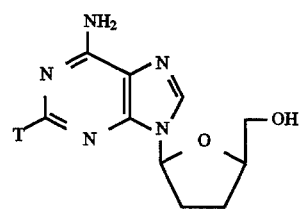

where T is F, Cl, Br or $NH_2$;

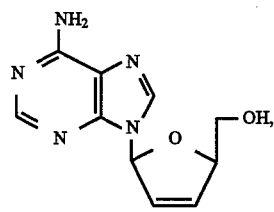

-continued

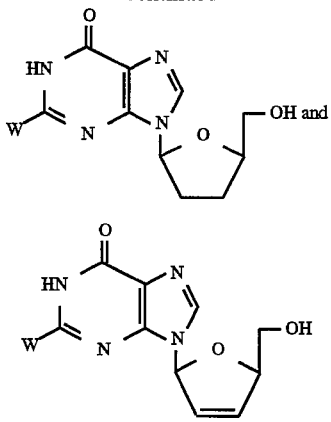

where W is H or NH₂.

In a first method aspect, the present invention relates to a method for inhibiting the growth or replication of Hepatitis B virus comprising exposing the virus to an inhibitory effective concentration of a compound according to the structure:

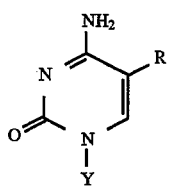

where Y is

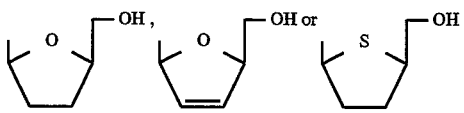

and R is H, F, Cl, Br, I or CH₃.

In this first method aspect, R is preferably H or F, most preferably H.

A second method aspect for inhibiting the growth or replication of Hepatitis B virus according to the present invention comprises exposing the virus to an inhibitory effective concentration of a compound according to the structure:

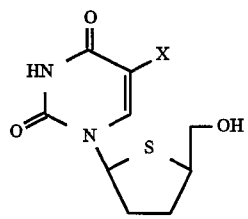

where X is H, F, Cl, Br, I, CH₃, —C≡CH, —HC=CH₂ or

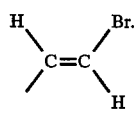

In this second method aspect, X is preferably H, F or CH₃, most preferably CH₃.

A third method aspect for inhibiting the growth or replication of Hepatitis B virus according to the present invention comprises exposing the virus to an inhibitory effective concentration of a compound according to the structure:

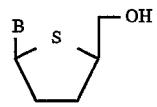

where B is

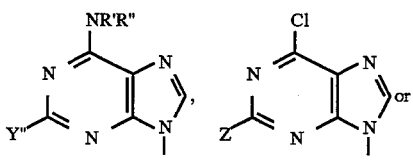

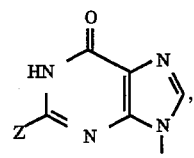

R' is H or CH₃;
R" is H or CH₃;
Y" is H, F, Br, Cl or NH₂ when R' and R" are H and
Y" is H when at least one of R' or R" is CH₃; and Z is H or NH₂.

In this third method aspect of the present invention, R' and R" are preferably H and Z is preferably NH₂.

A fourth method aspect for inhibiting the growth or replication of Hepatitis B virus according to the present invention comprises exposing the virus to an inhibitory concentration of a compound according to the structure:

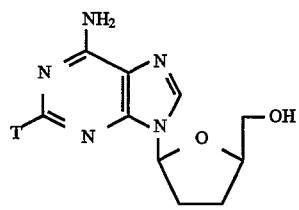

where T is H, F, Br, Cl or NH₂.

In this fourth method T is preferably H or F, most preferably H.

A fifth method aspect for inhibiting the growth or replication of Hepatitis B virus according to the present invention comprises exposing the virus to an inhibitory concentration of a compound according to the structure:

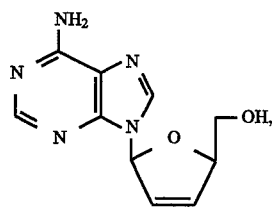

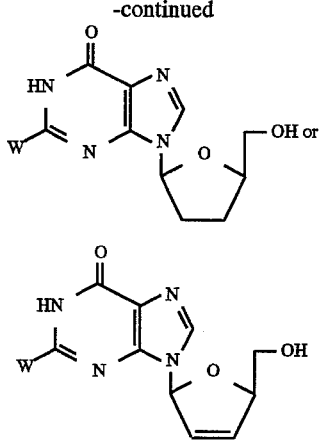

where W is H or NH$_2$.

The compounds according to the present invention are primarily useful for their anti-retroviral activity and in particular, their anti-HBV activity. The present compounds may also be useful for their biological activity as antifungal or antimicrobial agents. In addition, these compositions may also find use as intermediates in the chemical synthesis of other nucleoside or nucleotide analogs which are, in turn, useful as therapeutic agents or for other purposes. Preferably, these compositions find use as novel anti-HBV agents.

In general, the most preferred anti-viral, especially anti-HBV compounds, according to the present invention include those which are less cytotoxic to the host cells and more active to the targeted virus. Certain of the compounds, in pharmaceutical dosage form, may be used as prophylactic agents. These may be particularly appropriate as antiviral agents, and in particular, anti-HBV or anti-HIV agents.

The compounds according to the present invention are produced by synthetic methods which are readily known to those of ordinary skill in the art and include various chemical synthetic methods as elaborated in significantly more detail in the Examples which follow. In general, compounds according to the present invention are synthesized by condensing a previously synthesized nucleoside base onto the appropriate sugar synthon which will ultimately give rise to a nucleoside analog having the desired dideoxydbofuranosyl moiety of L-configuration. In certain instances, the synthetic pathway may deviate from the general synthetic pathway for a specific nucleoside analog (for example, in the case of 1-(2,3-dideoxy-beta-L-ribofuranosyl)cytosine and 1-(2,3-dideoxy-beta-L-ribofuranosyl)uracil as set forth in Example 1 and Scheme 3).

During chemical synthesis of the various compositions according to the present invention, one of ordinary skill in the art will be able to practice the present invention without undue experimentation. In particular, one of ordinary skill in the art will recognize the various steps that should be performed to introduce a particular substituent at the desired position of the base or a substituent at the desired position on the sugar moiety. In addition, chemical steps which are taken to "protect" functional groups such as hydroxyl or amino groups, among others, as well as "de-protect" these same functional groups, will be recognized as appropriate within the circumstances of the syntheses.

The therapeutic aspect according to the present invention relates to methods for treating retroviral infections in animal or human patients, in particular, HBV or HIV infections in humans comprising administering anti-vital effective amounts of the compounds according to the present invention to inhibit the growth or replication of the viruses in the animal or human patient being treated.

Pharmaceutical compositions based upon these novel chemical compounds comprise the above-described compounds in a therapeutically effective amount for treating a viral, preferably a Hepatitis B viral infection, optionally in combination with a pharmaceutically acceptable additive, carrier or excipient. One of ordinary skill in the art will recognize that a therapeutically effective amount will vary with the infection or condition to be treated, its severity, the treatment regimen to be employed, the pharmacokinetics of the agent used, as well as the patient (animal or human) treated.

In the pharmaceutical aspect according to the present invention, the compound according to the present invention is formulated preferably in admixture with a pharmaceutically acceptable carrier. In general, it is preferable to administer the pharmaceutical composition in orally-administrable form, but certain formulations may be administered via a parenteral, intravenous, intramuscular, transdermal, buccal, subcutaneous, suppository or other route. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the routineer's skill to modify the route of administration and dosage regimen of a particular compound in order to manage the pharmacokinetics of the present compounds for maximum beneficial effect in patients.

In certain pharmaceutical dosage forms, the pro-drug form of the compounds, especially including acylated (acetylated or other) derivatives, pyridine esters and various salt forms of the present compounds are preferred. One of ordinary skill in the art will recognize how to readily modify the present compounds to pro-drug forms to facilitate delivery of active compounds to a targeted site within the host organism or patient. The routineer also will take advantage of favorable pharmacokinetic parameters of the pro-drug forms, where applicable, in delivering the present compounds to a targeted site within the host organism or patient to maximize the intended effect of the compound.

The amount of compound included within therapeutically active formulations according to the present invention is an effective amount for treating the infection or condition, in its most preferred embodiment, for treating an HBV infection. In general, a therapeutically effective amount of the present compound in dosage form usually ranges from slightly less than about 1 mg./kg. to about 25 mg./kg. of the patient or considerably more, depending upon the compound used, the condition or infection treated and the route of administration. In the case of HBV infections, the compound is preferably administered in amounts ranging from about 1 mg/kg to about 25 mg/kg. This dosage range generally produces effective blood level concentrations of active compound ranging from about 0.04 to about 100 micrograms/cc of blood in the patient.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques.

For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

In particularly preferred embodiments according to the present invention, the compounds and compositions are used to treat retroviral infections of mammals and in particular humans. In its most preferred embodiment, the compounds are used to treat HBV infections, including chronic HBV infection. Generally, to treat HBV infections, the compositions will be administered in oral dosage form in amounts ranging from about 250 microgram up to about 500 mg. or more up to four times a day. The present compounds are preferably administered orally, but may be administered parenterally, topically or in suppository form.

The compounds according to the present invention, because of their unexpectedly low toxicity to host cells, may advantageously be employed prophylactically to prevent infection or to prevent the occurrence of clinical symptoms associated with the viral infection. Thus, the present invention also encompasses methods for the therapeutic or prophylactic treatment of viral infections, and in particular HBV infections. This prophylactic method comprises administering to a patient in need of such treatment an amount of a compound according to the present invention effective for alleviating, and/or preventing the vital infection. In the prophylactic treatment according to the present invention, it is preferred that the antiviral compound utilized should be as low in toxicity and preferably non-toxic to the patient. It is particularly preferred in this aspect of the present invention that the compound which is used should be maximally effective against the virus and should exhibit a minimum of toxicity to the patient.

In addition, compounds according to the present invention may be administered alone or in combination with other agents, especially including other compounds of the present invention. Certain compounds according to the present invention may be effective for enhancing the biological activity of certain agents according to the present invention by reducing the metabolism or inactivation of other compounds and as such, are co-administered for this intended effect. In a particularly preferred pharmaceutical composition and method for treating HBV infections, an inhibitory effective amount of 1-(2,3-dideoxy-beta-L-ribofuranosyl) cytosine and/or 1-(2,3-dideoxy-beta-L-ribofuranosyl) thymine is administered to a patient suffering from an HBV infection to alleviate the symptoms of such infection.

While not being limited by way of theory, it is believed that the compounds according to the present invention primarily induce their inhibitory effect on the growth or replication of HBV or HIV by functioning as antimetabolites of the reverse transcriptase enzyme of the virus.

The present invention is now described, purely by way of illustration, in the following examples. It will be understood by one of ordinary skill in the art that these examples are in no way limiting and that variations of detail can be made without departing from the spirit and scope of the present invention.

EXAMPLES

I. Chemical Synthesis of L-2'3'-dideoxynucleoside Analogs

Examples 1–9

In general, compounds of the present invention are synthesized according to the chemical synthetic method described hereinbelow. The synthetic chemical methodology employed to synthesize the present compounds represents modifications of literature procedures. The references from which a related chemical reaction have been modified to produce the present compounds are set forth in the examples, below.

Melting points were determined using a MelTemp apparatus and are uncorrected. Proton NMR spectra were recorded on a Varian EM390 or Bruker WM 250 instrument and reported as ppm (delta) downfield from $(CH_3)_4Si$. Ultraviolet spectra were recorded on a Beckman 25 spectrophotometer. Analytical thin-layer chromotography (TLC) was done using Merck EM Silica Gel 60 254 precoated sheets. Column chromatography employed Merck EM silica gel using standard organic solvents ($CH_2Cl_2$/MeOH or $CH_2Cl_2$/EtOAC varying in volume/volume ratio) unless otherwise indicated primarily to separate the alpha and beta anomeric mixtures.

EXAMPLE 1

Synthesis of 1-(2,3-Dideozy-beta-L-ribofuranosyl) cytosine, 1-(2,3-Dideoxy-beta-L-ribofuranosyl)-5-fluoro-, -5-bromo-, -5-chloro-,-5-iodo- and -5-methylcytosine The methodology of Taniguchi et al. (*Tetrahedron*, 30, 3532, 1974) and Farina et al. (*Tetrahedron Lett.*, 29, 1239, 1988) for the syntheses of D-ribose derivatives provided a model for our synthetic approach to the syntheses of the corresponding L-ribose derivatives. Nitrous acid deamination of D-glutamic acid (1) gave lactone 2, which was then converted to the corresponding ester 3 by treatment of compound 2, with ethanol and catalytic amount of p-toluenesulfonic acid (See Scheme 1). Reduction of compound 3 with $NaBH_4$ in ethanol gave (R)-4-(hydroxymethyl) -4-butyrolactone (4). Protection of the hydroxy group of compound 4 with tert-butyldimethylsilyl chloride in methylene chloride using imidazole as catalyst produced (R)-4-{[(tert-butyldimethylsilyl)oxy]methyl}-4-butyrolactone (5), which was then converted to the corresponding lactol 6 by reduction with diisobutylaluminum hydride (DIBAL) in toluene at −78° C. Acetylation of 6 with acetic anhydride and triethylamine afforded the key sugar intermediate, 1-O-acetyl-5-O-(tert-butyldimethylsilyl)-2,3-dideoxy-L-ribofuranose (7) as a mixture of alpha and beta anomers: MS, m/e 231 (M+—$CH_3CO$), 215 (M+—$CH_3COO$); NMR ($CDCl_3$)) delta 0.10 (s, 6H, $SiMe_2$), 0.95 (s, 9H, tert-butyl), 1.85–2.15 (m, 7H, $CH_2CH_2$ and $COCH_3$), 3.50–3.65 (M, 2H, 5'-H), 4.10–4.30 (m, 1H, 4'-H), 6.20–6.30 (m, 1H, 1'-H).

Uracil, 5-fluoro, 5-bromo-, 5-chloro- and 5-iodouracil as well as thymine were coupled with acetate 7 by the methodology of Okabe et al. (*J. Org. Chem.*, 53, 4780, 1988) with minor modifications.

Silylated 5-fluorouracil, prepared from 5-fluorouracil, (4.3 g, 33 mmol) was reacted with acetate 7 (8.3 g, 30 mmol) and ethylaluminum dichloride (16.7 ml, of a 1.8M solution in toluene, 30 mmol) in methylene chloride at room temperature for 3 hrs. to give 8.5 g (83%) of 1-{5-O(tert-butyldimethylsilyl)-2,3-dideoxy-alpha, beta,-L-ribofuranosyl]-5-fluorouracil (8,R=F) as a 2:3 alpha/beta anomeric mixture. The alpha and beta anomers were separated by silica gel chromatography. The beta anomer (9): NMR ($CDCl_3$) delta 0.10 (s, 6H, $SiMe_2$), 0.95 (s, 9H, tert-butyl), 1.80–2.45 (m, 4H, 2'-H and 3'-H), 3.50–3.70 (m, 1H, 4'-H), 3.95–4.15 (m, 2H, 5'-H), 5.90–6.05 (m, 1H, 1'-H), 8.10–8.20 (d, 1H, 6-H), 9.30–9.50 (br, 1H, NH, $D_2O$ exchangeable); the alpha isomer: NMR ($CDCl_3$) delta 0.10 (s, 6H, $SiMe_2$), 0.95 (s, 9H, tert-butyl), 1.90–2.55 (m, 4H, 2'-H and 3'-H), 3.60–3.65 (m, 2H, 5'-H), 4.30–4.50 (m, 1H, 4'-H), 5.90–6.05 (m, 1H, 1'-H), 7.30–7.40 (d, 1H, 6-H), 9.00–9.30 (br, 1H, NH, $D_2O$ exchangeable). Treatment of the beta anomer (9, 3 g, 8.7 mmol) with 4-chlorophenyl phosphorodichloridate (6.2 mL, 37.8 mmol) and 1,2,4-triazole (7.9 g, 114 mmol) in anhydrous pyridine (60 ml,) at room temperature yielded the 4-triazolylpyrimidinone derivative 10. The crude product 10 was treated with a mixture of ammonium hydroxide/dioxane (1:3, v/v) to afford the 2',3'-dideoxycytidine drivative 11 (1.2 g, 40%), which was then deblocked by reaction with tetra-n-butylammonium fluoride in THF at room temperature for 20 min to afford the target compound 1-(2,3-dideoxy-beta-L-ribofuranosyl)-5-fluorocytosine (12, R=F, L-FDDC): mp 147°–149° C.; NMR (DMSO-$d_6$) delta 1.85–2.35 (m, 4H, 2'-H and 3'-H), 3.60–3.82 (m, 2H, 5'-H), 4.25 (m, 1H, 4'-H), 5.15 (t, 1H, 5'-OH, $D_2O$ exchangeable), 5.95–6.15 (m, 1H, 1'-H), 7.45 (br s, 2H, 4-$NH_2$, $D_2O$ exchangeable), 8.22 (d, 1H, 6-H).

To synthesize 1-(2,3-dideoxy-beta-L-ribofuranosyl) cytosine, 1-(2,3-dideoxy-beta-L-ribofuranosyl) -5-bromo-, -5-chloro-, -5-iodo-, or -5-methylcytosine, the analogous procedure used to synthesize the 5-fluoro derivative was employed. For the coupling reaction, the corresponding silylated 5-bromo-, -5-chloro-, -5-iodo-, or -5-methylcytosine was used instead of 5-fluorouracil. All other steps are analogous to those for the synthesis of the 5-fluoro derivatitve 12 (R=F).

Treatment of compound 9 with tetra-n-butylammonium fluoride in THF gave the corresponding uracil derivative 13.

Compound 12 (R=H,F,Cl,I and $CH_3$) was also synthesized by an alternative methodology (See Scheme 2), by which the silylated compound 15 (R=H,F,Cl,I and $CH_3$), prepared from the corresponding cytosine (14, R=H) and its derivatives 14 (R=F,Cl,I and $CH_3$), were directly coupled with acetate 7, followed by separation of the alpha and beta anomers 16 and removal of the protecting group.

Compound 12 (R=H) was also synthesized by a stereospecific approach (See Scheme 3), in which the possibility of producing the alpha anomer was eliminated. O-2, 2'-Anhydrouridine 19 was prepared by the method of Holy (*Collection Czechoslov. Chem. Commun.*, 37, 4072, 1972) from L-arabinose (17) via the intermediate oxazoline derivative 18. Treatment of compound 19 with tert-butyldimethylsilyl chloride in pyridine gave the protected chloro derivative, 1-[5-O(-tert-butyldimethylsilyl)-2-chloro-2-deoxy-beta -L-ribofuranosyl]uracil (20, R=H). Conversion of compound 20 to the corresponding 2',3'-unsaturated nucleoside 22 was achieved by previously developed methodology (Lin et al., *Tetrahedron Lett.*, 31, 3829, 1991). Treatment of compound 20 with phenyl chlorothionocarbonate and 4-dimethylaminopyridine in acetonitrile under nitrogen at room temperature yielded the 2'-chloro-3'-O-phenoxythiocarbonyl derivative 21, which has two different vicinal groups at the 2'-and 3'-positions. Reduction of compound 21 with tri-n-butyltin hydride and azobisisobutyronitrile (AIBN) in dry toluene at 60°–70° C. for 4h produced the 2',3'-unsaturated derivative 22 as a foam: NMR ($CDCl_3$) delta 0.10 (s, 6H, $SiMe_2$), 0.95 (s, 9H, tert-butyl), 3.90 (m, 2H, 5'-H), 4.90 (m, 1H, 4'-H), 5.65–5.75 (d, 1H, 5-H), 5.80–5.90 (d, 1H, 3-H), 6.25–6.35 (d, 1H, 2'-H), 7.05–7.10 (m, 1H, 1'-H), 7.75–7.85 (d, 1H, 6H), 9.55 (s, 1H, —NH, $D_2O$ exchangeable). Catalytic hydrogenation of compound 22, followed by treatment with 4-chlorophenyl phosphorodichloridate and 1,2,4-triazole yielded the 4-triazolylpyrimidinone derivative 24, which was then converted to the desired 1-(2,3-dideoxy-beta-L-ribofuranosy) cytosine 12 (R=H, L-DDC) by treatment of 24 with $NH_4OH$/dioxane, followed by deblocking of the 5'-protecting group as previously described.

Compound 12 (R=H, L-DDC): mp 194°–196° C.; $^1HNMR$ (DMSO-$d_6$) 1.74–2.24 (m, 4-H, 2'-H and 3'-H), 3.49–3.65 (m, 2H, 5'-H), 3.98–3.99 (m, 1H, 4'-H), 4.96–5.00 (t, 1H, 3'-OH, $D_2O$ exchangeable), 5.65–5.68 (d, 1H, 5-H), 5.85–5.93 (m, 1H, 1'-H), 7.01–7.06 (m 2H, —$NH_2$, $D_2O$, exchangeable), 7.87–7.90 (d, 1H, 6-H).

Treatment of compound 23 with tetra-n-butylammonium fluoride in THF gave the corresponding uracil derivative 13 (R=H): $^1HNMR$ (DMSO-$d_6$) delta 1.80–2.05 (m, 4-H, 2'-H and 3'-H), 3.45–3.60 (m, 2H, 5'-H), 3.85–4.05 (m, 1H, 4'-H), 4.85–5.00 (t, 1H, 5'-OH, $D_2O$ exchangeable), 5.45–5.55 (d, 1H, 5-H), 5.80–6.00 (m, 1H, 1'-H), 7.80–1.90 (d, 1H, 6-H), 11.10 (s, 1H, NH, $D_2O$ exchangeable).

EXAMPLE 2

2',3'-Dideoxy-, 2',3'-Dideoxy-N-methyl- and 2',3'-Dideoxy-N,N-dimethyl-beta-L-adenosine, and 2',3'-Dideoxy-L-inosine and 2',3'-Dideoxy-beta-L-guanosine The synthesis of 2',3'-dideoxy-, 2'3'-dideoxy-6-N-methyl-, and 2',3'-dideoxy-N,N-dimethyl-beta-L-adenosine, and 2',3'-dideoxy-beta-L-inosine and 2',3'-dideoxy-beta -L-guanosine (See Scheme 4) was based on the methodology reported by Fujimori et al. (*Nucleoside & Nucleotides*, 11, 341, 1992) for the synthesis of purine 2'-deoxynucleosides. Treatment of 6-chloropurine with NaH (60% in oil, washed with n-hexane) and acetate 7 in anhydrous acetonitrile under argon produced 6-chloro-9-[(5-O-tert-butyldimethylsilyl)-2,3-dideoxy-beta-L-erythro-pentofuranosyl]purine (26) together with the corresponding N-7 glycosyl isomer, which was separated by silica gel chromatography. Subsequent treatment of compound 26 with $NH_3/CH_3OH$, $CH_3NH_2/CH_3OH$, or $(CH_3)_2NH$/

CH₃OH at elevated temperature, followed by deprotection with tetra-n-butylammonium fluoride in THF afforded 2',3'-dideoxy-L-adenosine (27, R=R'=H), 2',3'-dideoxy-N-methyl-beta-L-adenosine (27, R=H, R'=CH₃,) and 2'3'-dideoxy-N,N-dimethyl-beta-L-adenosine (27, R=R'=CH₃), respectively. Treatment of compound 26 with tetra-n-butylammonium fluoride in THF, followed by alkaline hydrolysis of the deblocking nucleoside (28) with 2 N KOH/dioxane (1:1, v/v) gave 2'3'-dideoxy-L-inosine (29). Similarly, treatment of 2-amino-6-chloropurine with NaH (60% in oil, washed with n-hexane) and acetate 7 in anhydrous acetonitrile under argon afforded 2-amino-6-chloro-9-[(5-O-tert-butyldimethylsilyl)-2,3-dideoxy-beta-L-erythro-pentofuranosyl]purine (30). Conversion of compound 30 to the final product, 2'3'-dideoxy-beta-L-guanosine (32) was achieved via the intermediate 31 by deblocking with tetra-n-butylammonium fluoride in THF and alkaline hydrolysis with 2N KOH/dioxane (1:1,v/v).

EXAMPLE 3

2-Chloro-, 2-Bromo-, 2-Amino-, and 2-Fluoro-2',3'-dideoxy-beta-L-adenosine

These compounds are synthesized as described in Scheme 5 by the methodology employed in Example 2. 2,6-dichloropurine, prepared by the method described by Elion and Hitching (J. Am. Chem. Soc., 78, 3508, 1956) was treated with NaH (60% in oil, washed with n-hexane) and acetate 7 in anhydrous acetonitrile under argon to give 2,6-dichloro-9-[(5-O-tert-butyldimethylsilyl)- 2,3-dideoxy-beta-L-erythro-pentofuranosyl]purine (33) and the corresponding N-7 glycosyl isomer, which was separated by silica gel chromatography. Treatment of compound 33 with NH₃/CH₃OH at elevated temperature, followed by deprotection with tetra-n-butylammonium fluoride in THF afforded 2-chloro-2',3'-dideoxy-L-adenosine (34). Treatment of dibromopurine with NaH (60% in oil, washed with n-hexane) and acetate 7 in anhydrous acetonitrile under argon to produce 6-bromo-9-[(5-O-tert-butyldimethylsilyl)-2,3-dideoxy-beta-L-erythro-pentofuranosyl]purine (31) together with the corresponding N-7 glycosyl isomer, which was separated by silica gel chromatography. Subsequent treatment of compound 31 with NH₃/CH₃OH at elevated temperature, followed by deprotection with tetra-n-butylammonium fluoride in THF afforded 6-bromo-(2,3-dideoxy-beta-L-erthro-pentofuranosyl)purine (41). 2,6-Bis(benzamido)purine, prepared by the method described by Davoll and Lowy (J. Am. Chem. Soc., 73, 1650, 1951) was treated with NaH (60% in oil, washed with n-hexane) and acetate 7 in anydrous acetonitrile under argon produced 2,6-bis(benzamido)-9[(5-O-tert-butyldimethylsilyl)-2,3-dideoxy-beta-L-erythro-pentofuranosyl]purine (37), which was then subsequently deblocked by reaction with tetra-n-butylammonium fluoride in THF and sodium ethoxide in ethanol to give 2-amino-2',3'-dideoxy-beta-L-adenosine (38). Treatment of compound 38 with sodium nitrite and 48–50% fluoroboric acid below −10° C. yielded 2-fluoro-2',3'-dideoxy-beta-L-adenosine (39).

EXAMPLE 4

1-(2,3-Didehydro-dideoxy-beta-L-ribuofuranosyl) cytosine, 1-(2,3-Didehydro-dideoxy-beta-L-ribofuranosyl)-5-fluoro-, -5-bromo-, -5-chloro-, -5-iodo-, and -5-methylcytosine These compounds were synthesized as set forth in Scheme 6 by a methodology developed for the syntheses of the related D-isomers (Lin, et al., Biochem. Phamacol., 36, 311, 1987; Lin, et al., Organic Preparations and Procedures Intl., 22, 265, 1990). Treatment of 2'-deoxy-L-uridine (40, R=H), was prepared by the procedure of Holy (Collection Czechoslov. Chem. Commun., 37, 4072, 1972), with 2 equivalents of methanesulfonyl chloride in dry pyridine at −5° to 0° C. gave the 3',5' di-O-mesyl derivative (41, R=H). Conversion of compound 41 (R=H) to 2'-deoxy-3',5'-epoxy-beta-L-uridine (43, R=H) via the intermediate anhydronucleoside 42 (R=H) by treatment with 1N NaOH according the procedure of Horwitz et al. (J. Org. Chem., 32, 817, 1967). Treatment of compound 43 (R=H) with 1,2,4-triazole and 4-chlorophenyl phosphorodichloridate in dry pyridine yielded the 4-triazolylpyrimidinone 44 (R=H), which was then reacted with NH₄OH/dioxane to give the cyridine derivative 45 (R=H). Treatment of compound 45 (R=H) with potassium t-butoxide in DMSO afforded the final product 1-(2,3-didehydro-2,3-dideoxy-beta-L-ribofuranosyl)cytosine (46, R=H): ¹HNMR (DMSO-d₆) delta 3.50 (m, 2H, 5'-H), 4.72 (m, 1H, 4'-H), 4.92 (br s, 1H, 5'-OH, D₂O exchangeable), 5.64 (d, 1H, 5-H), 5.83 (m, 1H, 3'-H), 6.30 (m, 1H, 2'-H), 6.85 (m, 1H, 1'-H), 7.09–7.15 (br d, 2H, 4-NH₂, D₂O exchangeable), 7.64 (D, 1H, 6-H).

EXAMPLE 5

2',3'-Didehydro-2',3'-dideoxy-beta-L-adenosine

2',3'-Didehydro-2',3'-dideoxy-beta-L-adenosine (51) was synthesized as shown in Scheme 7 by the methodology of Barton et al. (Tetrahedron, 49, 2793, 1993) and Chu et al. (J. Org. Chem., 54, 2217, 1989) for the preparation of the D-isomer. Treatment of L-adenosine (47) with tert-butyldimethlsilyl chloride and imidazole in dry DMF with exclusion of moisture for 20 hr gave 5'-O-(tert-butyldimethylsilyl)-beta-L-adenosine (48), which was then reacted with CS₂, 5 N NaOH solution, and CH₃I in DMSO to afford the 2',3'-O-bis(dithiocarbonate) derivative 49. Deoxygenation of 49 with triethylsilane and benzoyl peroxide under argon, followed by deprotection of the olefin derivative 50 with tetra-n-butylammonium fluoride in THF afforded the final product 51.

Synthesis of the corresponding 2',3'-Didehydro-2',3'-dideoxy-beta-L-guanosine and 2',3'-Didehydro-2',3'-dideoxy-beta-L-inosine analogs followed the same procedure as above, starting from L-guanosine and L-inosine respectively.

EXAMPLE 6

1'-(2,3-Dideoxy-4-thio-beta-L-ribofuranosyl) cytosine, 1-(2,3-Dideoxy-4-thio-beta-L-ribofuranosyl)-5-fluoro-,-5-chloro-, -5-bromo-, -5-iodo-, and -5-methylcytosine The methodology of Secrist et al. (J. Med Chem., 35, 533, 1922) for the synthesis of 2',3'-dideoxy-4'-thio-D-nucleosides provided a useful example for our synthetic approach to the synthesis of 1-2',3'-dideoxy-4'-thio-beta-L-nucleoside analogs (See Scheme 8).

D-glutamic acid (1) was treated with sodium nitrite in hydrochloric acid to produce (R)-1,4-butyrolactone-4-carboxylic acid (2). Compound 2 was then reduced by borane-dimethyl sulfide complex in THF to give the corresponding (R)-4-(hydroxymethyl)-4-butyrolactone (4), which was subsequently treated with tert-butyldiphenylsilyl chloride in methylene chloride using imidazole as a catalyst to afford (R)-5-O-tert-butyldiphenylsilyl-4-hydroxymethyl- 1,4-butyrolactone (53). The protected lactone 53 was opened with sodium hydroxide in ethanol and then converted to the methyl ester of 5-[(tert-butyldiphenylsilyl)oxy]4-(R)-hydroxypentanoic acid (54) by reaction with dimethyl sulfate in dimethyl sulfoxide. Compound 54 was transformed into the methyl ester of 5-[(tert-butyldiphenylsilyl)oxy]-4-(S)-iodopentanoic acid (55) by treatment with triphenylphosphine, imidazole and iodine. Displacement of the iodo group in compound 55 by thioacetate in toluene occurred readily to give the methyl ester of 4-(R)-(acetylthio)-5-[(tert-butyldiphenylsilyl)oxy]pentanoic acid (56). Compound 56 was then treated with 2 equivalents of diisobutylaluminum hydride (DIBAL) in toluene to reductively deprotect the sulfur and reduce the methyl ester to an aldehyde, thereby producing the thiolactol via spontaneous cyclization. The thiolactol was acetylated with acetic anhydride in pyridine to give 1-O-acetyl-5-O-(tert-butyldiphenylsilyl)-2,3-dideoxy-4-thio-L-ribofuranose (57): $^1$HNMR (CDCl$_3$) delta 7.67 (m, 4H, ArH), 7.40 (m, 6H, ArH), 6.10 (m, 1H, 1-H), 3.70 (m, 1H, 4-H), 3.52 (m, 2H, 5-H), 2.20 (m, 2H, CH$_2$), 2.00 (2 s, 3H, CH$_3$CO), 1.92 (m, 2H, CH$_2$), 1.08 (s, 9H, tert-butyl).

Cytosine, 5-fluorocytosine, and the other 5-substituted cytosine derivatives were coupled with the acetate 57 by the methodology of Vorbruggen and Bennua (*J. Org. Chem.*, 39, 3654, 1974) with modifications. A mixture of cytosine (0.42 g, 3.80 mmol), hexamethyldisilazane (HMDS, 0.54 mL, 2.52 mmol), chlorotrimethylsilane (TMSCl 1.48 mL, 11.6 mmol), potassium nonafluorobutanesulfonate (3.08 g, 8.9 mmol), and the acetate 57 (1.04 g, 2.52 mmol) in dry acetonitrile was stirred at room temperature overnight to afford 0.65 g (55%) of 1-[5-O-(tert-butyldiphenylsilyl)-2,3-dideoxy-4-thio-alpha,beta-L-ribofuranosyl]cytosine (58 X═H) as a 4:3 alpha/beta- mixture. The alpha and beta anomers were separated by silica gel column chromatography. Deprotection of 58 (beta anomer) afforded 1-(2,3-dideoxy-4-thio-beta-L-ribofuranosyl)cytosine (59 X═H) in 60% yield: MS m/e 228 (M$^+$+1); $^1$HNMR (DMSO-d$_6$) delta 8.05 (d, 1H, H-6), 7.08 (br d, 2H, NH$_2$, D$_2$O exchangeable), 6.10 (m, 1H, 1'-H), 5.70 (d, 1H, H-5), 5.20 (br d, 1H, 5'-OH, D$_2$O exchangeable), 3.58 (m, 1H, 5'-H), 3.52 (m, 2H, 4'-H and 5'-H), 2.20 (m, 1H, 2'-H), 2.04 (m 2H, 2'-H and 3'-H), 1.88 (m, 1H, 3'-H).

EXAMPLE 7

1-(2,3-Dideoxy-4-thio-beta-L-ribofuranosyl)-5-methyl-, -5-ethyl-, -5-vinyl-, -5-bromovinyl-, -5-ethynyl-, -5-fluoro-, -5-chloro-, -5-bromo-, -5-iodouracil, and 1-(2,3-Dideoxy-4-thio-beta-L-ribofuranosyl)uracil Thymine, uracil, -5-ethyl-, -5-vinyl-, -5-bromovinyl-, -5-ethynyl-, -5-fluoro-, -5-chloro-, -5-bromo-, -5-iodouracil, and other 5-substituted uracil derivatives were coupled with 1-O-acetyl-5-O-(tert-butyldiphenylsilyl)-2,3-dideoxy-4-thio-L-ribofuranose (57) using the same procedure as described in Example 6 to give the respective 5-subsituted pyrimidine nucleosides.

A mixture of the acetate 57 (1.40 g, 3.32 mmol), thymine (0.52 g, 4.20 mmol), HMDS (0.70 mL, 3.32 mmol), TMSCl (1.60 ml, 12.8 mmol) and potassium nonafluorobutane-sulfonate (3.50 g, 10.16 mmol) in dry acetonitrile was stirred at 25° C. overnight under nitrogen to give 1-[5-O(tert-butyldiphenylsilyl)-2,3-dideoxy-4-thio-alpha,beta-L-ribofuranosyl]thymine (60, X═CH$_3$) 1.18 g (74%) as a 4:3 alpha/beta anomeric mixture. The alpha/beta anomers were separated by silica gel column chromatography. Deprotection of beta-anomer 60 afforded 1-(2,3)-dideoxy-4-thio-beta-L-ribofuranosyl)thymine (61, X═CH$_3$) in 55% yield: Ms m/e 243 (m$^+$+1), $^1$HMR (DMSO-d$_6$) delta 11.5 (br s, 1H, NH), 7.74 (s, 1H, 6-H), 6.11 (m, 1H, 1'-H), 5.00 (t, 1-H. 5'-OH, D$_2$O exchangeable), 3.70 (m, 1-H, 4'-H), 3.65 (m, 2H, 5'-CH$_2$) 2.20–1.80 (m, 4H, 2'-CH$_2$ and 3'-CH$_2$), 1.79 (s, 3H, 5-CH$_3$).

EXAMPLE 8

2',3'-Dideoxy-4'-thio-beta-L-adenosine, 2',3'-Dideoxy-4'-thio-N-Methyl-beta-L-, -N,N-dimethyl-beta-L-adenosine, 2',3'-Dideoxy-4'-thio-beta-L-inosine, and 2',3'-Dideoxy-4'-thio-beta-L-guanosine 2',3'-Dideoxy-4'-thio-beta-L-adenosine, 2'3'-Dideoxy-4'thio-N-methyl-beta-L-adenosine, 2'3'-Dideoxy-4'thio-N, N-dimethyl-beta-L-adenosine, 2',3'-Dideoxy-4'-thio-beta-L-inosine, and 2',3'-Dideoxy-4'-thio-beta-L-guanosine were synthesized by the similar methodology of Secrist et at. (*J Med Chem.*, 35, 533, 1992) for the syntheses of 2',3'-dideoxy-4'-thio-D-nucleosides.

Sugar 57 (4.3 g, 10.4 mmol) was coupled with 6-chloropurine (2.4 g, 15.6 mmol) in the presence of diethylaluminum chloride (5.9 mL, 10.6 mmol) in acetonitrile (150 mL) at 0°–5° C. for 2h, by the procedure of Niedballa and Vobruggen (*J. Org. Chem.*, 39, 3654, 1974), to give 2.81 g (53%) of 9-[5-O-(tert-butyldiphenlsilyl)-2,3-dideoxy-4-thio-alpha, beta-L-ribofuranosyl]-6-chloropyrine as a 1:1 alpha/beta anomeric mixture. The alpha and beta anomers were separated by silica gel column chromatography. The beta-anomer 62 was treated with saturated ammonia/methanol and then deprotected with 1M tetrabutylammonium fluoride and THF to afford 2',3'-dideoxy-4'-thio-beta-L-adenosine (63, R'═R"═H): $^1$HNMR (DMSO-d$_6$) delta 8.30 (s, 1H, 2-H), 8.10 (s, 1H, 8-H), 7.30 (s, 2H, NH$_2$, D$_2$O exchangeable), 6.12 (m, 1H, 1'-H), 5.11 (br s, 1H, 5'-OH, D$_2$O exchangeable), 3.70 (m, 3H, 5'-CH$_2$, 4'-H), 2.42 (m, 2H, 2'-CH$_2$), 2.13 (m, 1H, 3'-H), 2.00 (m, 1H, 3'-H).

Compound 62 was deprotected with 1M tetrabutylammonium fluoride and THF to yield 9-(2,3-dideoxy-4'-thio-beta-L-fibofuranosyl)-6-chloropurine (64). Alkaline hydrolysis (Fujimori, et al., *Nucleosides & Nucleosides*, 11, 341, 1992) of the 6-chloro moiety in compound 64 afforded 2',3'-dideoxy-4'-thio-beta-L-inosine (65) in 45% yield: MS m/e 253 (m$^+$+1); $^1$HNMR (D$_2$O) delta 8.52 (s, 1H, 2-H), 8.19 (s, 1H, 8-H), 6.10 (m, 1H, 1'-H), 3.94 (m, 1H, 5'-H), 3.75 (m, 2H, 5'-H, 4'-H), 2.52 (m, 2H, 2'-CH$_2$), 2.30 (m, 1H, 3'-H) 1.92 (m, 1H, 3'-H).

2',3'-Dideoxy-4'-thio-beta-L-guanosine (68) was synthesized from acetate (57) by the similar methodology as described for the synthesis of compound 65: MS m/e 268 (m$^+$+1): $^1$HNMR (DMSO-d$_6$) delta 10.7 (br s, 1H, NH, D$_2$O exchangeable), 8.01 (s, 1H, 8-H), 6.55 (s, 2H, NH$_2$, D$_2$O exchangeable), 5.90 (m, 1H, 1'-H), 5.09 (br s, 1H, 5'-OH, D$_2$O exchangeable), 3.70 (m, 1H, 4'-H), 3.50 (m, 2H, 5'-H), 2.36 (m, 2H, 2'-H), 2.17 (m, 1H, 3'-H), 1.93 (m, 1H, 3'-H).

EXAMPLE 9

2',3'-Dideoxy-4'-thio-2-chloro-beta-L-adenosine, -2-amino-beta-L-adenosine, -2-fluoro-beta-L-adenosine, -2-chloro-N-methyl-beta-L-adenosine, -2-chloro-N,N-dimethyl-beta-L-adenosine, -2-bromo-beta-L-adenosine, -2-bromo-N-methyl-beta-L-adenosine and -2-bromo-N,N-dimethyl-beta -L-adenosine 2',3'-Dideoxy-4'-thio-2-chloro-beta-L-adenosine, 2-amino-beta-L-adenosine,-2-fluoro-beta-L-adenosine, -2-chloro-N-methyl- beta-L-adenosine, -2-chloro-N,N-dimethyl-beta-L-adenosine, -2-bromo-beta-L-adenosine, -2-bromo-N-methyl-beta-L-adenosine and -2-bromo-N,N- dimethyl-beta-L-adenosine and other beta-L-adenosine derivatives were synthesized as set forth in Scheme 11.

9-[5-O-(tert-Butyldiphenylsilyl)-2,3-dideoxy-4-thio-beta-L-ribofuranosyl]-2,6-dichloropurine (69) was synthesized from the acetate 57 and 2,6-dichloropurine by the similar methodology as described for the synthesis of compound 62 in an approximate 2:3 alpha/beta anomer ratio in 60% yield. The alpha and beta anomers were separated by silica gel column chromatography. Compound 69 was treated with saturated ammonia/methanol and then deprotected with 1M tetrabutylammonium fluoride in to provide 2',3'-dideoxy-4'-thio-2-chloro-beta-L-adenosine (70 R'=R"=H) in 52% yield: MS m/e 286 (m$^+$+1); $^1$HNMR (DMSO-d$_6$) delta 8.46 (s, 1H, 2-H), 7.82 (br s, 2H, NH$_2$, D$_2$O exchangeable), 6.10 (m, 1H, 1'-H), 5.10 (m, 1H, 5'-OH, D$_2$O exchangeable), 3.74 (m, 1H, 4'-H), 3.60 (m, 2H, 5'-H), 2.42 (m, 2H, 2'-H), 2.13 (m, 1H, 3'-H), 2.02 (m, 1H, 3'-H). 2',3'-Dideoxy-4'thio-2-bromo-alpha,beta-L-adenosine (72, R'=R"=H) was synthesized by coupling the acetate 57 and 2,6-dibromopurine, followed by treatment of the respective amine by the same methodology as described for the synthesis of compound 70.

Compound 69 was treated with lithium azide to give the diazido nucleoside 73, which was then reduced with lithium aluminium hydride (LAH) to produce 9-[5-O-(tert-butydiphenylsilyl)-2,3-dideoxy-4-thio-alpha-beta-L-ribofuranosyl]-2,6-diaminopurine (74). Compound 74 was deprotected with tetrabutylammonium fluoride in THF to yield 2',3'-dideoxy-4'-thio-2-amino-alpha,beta-L-adenosine (75), which was then converted to 2',3'-dideoxy-4'-thio-2-fluoro-alpha,beta-L-adenosine (76) by reaction with sodium nitrite and HBF$_4$.

II. Biological Activity

A. Anti-HBV Effects

The biological activity of the present compounds was assessed as described by Doong, S-L, et al., *Proc. Natl. Acad Sci. U.S.A* 88, 8495–8499 (1991). The human hepatoma cell line carrying the HBV (designated 2.2.15) kindly provided by Dr. G. Acs was used in the study. Price, et at., *Proc. Natl. Acad Sci. U.S.A.* 86, 8541 (1989). Briefly, Six day-old cultures were treated with varying concentrations of the drug in the culture medium (Minimum essential medium with Earl's salts and 10% fetal bovine serum). The drug was left in the culture medium for a period of 3 days after which period the medium was aspirated and fresh medium containing the same concentration(s) of the drug was added. At the end of the subsequent 3 day period the culture medium was harvested. The culture medium was processed for obtaining the ions by the polyethylene glycol precipitation method (Doong, et at., supra). Viral DNA thus recovered from the secreted particles was subjected to Southern analysis. Inhibition of the viral replication was determined by the comparison of the viral DNA from drug-treated versus control cultures not treated with the drug.

To determine the cellular toxicity of the present compounds, the T-lymphoblastoic cell line (CEM) was used. Cells were subjected to varying concentrations of the drug(s) and cell numbers were determined 3 days post treatment by the method described by Chen, C-H and Cheng, Y-C *J. Biol. Chem.*, 264, 11934 (1989). Concentrations of the drug which would result in 50% killing of the cell populations were determined from the plot generated by representing cell numbers corresponding to the individual drug concentrations.

The effects of the various drag concentrations on mitochondrial DNA (mt DNA) was evaluated by the method described by Chen and Cheng, supra. GEM cells treated with varying concentrations of the drug were collected by centrifugation. After washing the cells with phosphate buffered saline, cells were lysed by suspending the cells in 10 mM Tris-HCl (pH 7.0) and repeating freeze thaw cycles. The resulting cells were then subjected to RNase A treatment at a final enzyme concentration of 10 ug/ml, followed by proteinase K treatment (100 ug/ml) for 1 hour. The DNA thus obtained by this procedure was then immobilized on nylon membrane after the addition of 0.8 vol of NaI and boiling for 10 minutes. Hybridization of the resulting DNA to a mt DNA specific probe was performed by following the method of Doong, S-L, supra and autoradiography was also performed. Quantitative estimates were obtained by scanning densitometer. The blots were stripped of the mtDNA probe and rehybridized to human Alu sequence probe to determine the amounts of DNA for normalization and estimation of absolute amounts of the mt DNA.

B. Anti-HIV Effects

Anti-HIV effects were determined using the T-lymphoblastoid cell line, MT-2 infected with the HIV-1 virus. The inhibition was determined by the method of Larder, B. A., et al., *Antimicrob. Agents Chemother.*, 34, 436 (1990).

It is to be understood by those skilled in the art that the foregoing description and examples are illustrative of practicing the present invention, but are in no way limiting. Variations of the detail presented herein may be made without departing from the spirit and scope of the present invention as defined by the following claims.

C. Results of Biological Testing

Analysis of the vital replication of HBV from the secreted particles revealed that the DNA replication was efficiently inhibited by L-ddC. The ID$_{50}$ concentration required to inhibit the viral replication by this compound was 0.01 uM. The cellular cytotoxicity of this compound as compared to ddC was also considerably less as evidenced by the table 1 set forth below. It is interesting to note that this compound has several fold higher activity against HBV with minimal cellular effects, an unexpected result. ddC, on the other hand, was much more cytotoxic than L-ddC. In addition, ddC also was shown to exhibit significant effects on host mitochonrial DNA. It is expected that L-ddC would have significantly lower adverse effects on the mitochondrial DNA than ddC as concentrations as high as 100 uM of L-ddC were not inhibitory in the assay. Based upon these results, L-ddC is an extremely interesting compound with predominantly anti-HBV activity, and a clear advance in the art. The data on the effects of L-ddC are summarised in Table 1, below.

TABLE 1

| Compound | Cyto-toxicity | Anti-mitochondrial DNA ID$_{50}$(uM) | Anti-HBV | Anti-HIV |
|---|---|---|---|---|
| ddC* | 10 | 0.022 | 2.8 | 1 |
| (—)S-ddC* | 50 | >50 | 0.01 | 2 |
| L-ddC | 54 ± 20 | >100 | 0.01 | 8 |

*Data from Published Literature:
Mathes, et al., Antimicrob. Agents Chemother., 34, 1986 (1990);
Lee, et al., Antimicrob. Agents Chemother., 33, 336 (1989);
Meisel, et al., Med. Virol., 30, 137 (1990); Mathes, et al.,
Antimicrob. Agents Chemother., 35, 1254 (1991); Yokota, et al.,
Antimicrob. Agents Chemother., 34, 1326 (1990); Price, et al.,
Proc. Natl. Acad. Sci. U.S.A., 86, 8541 (1989); Suzuki, et al.,
Biochem. Biophys. Res. Commun., 156, 1144 (1988); Doong, S-L,
et al., Proc. Natl. Acad. Sci. U.S.A., 88, 8495 (1991); Chang,
C-H, et al., J. Biol. Chem., 267, 22414 (1992); Chen, C-H, et al.,
J. Biol. Chem., 264, 11934 (1989).

Utilizing the above-described procedures, other compounds according to the present invention are screened for anti-HBV activity, and anti-HIV. The compositions according to the present invention are tested and these compounds exhibit significant anti-viral activity.

It is to be understood by those skilled in the art that the foregoing description and examples are illustrative of practicing the present invention, but are in no way limiting. Variations of the detail presented herein may be made without departing from the spirit and scope of the present invention as defined by the following claims.

We claim:

1. The compound 1-(2,3-Dideoxy-beta-L-ribofuranosyl)-5-fluorocytosine.

2. A pharmaceutical composition comprising a therapeutically effective amount of the compound 1-(2,3-Dideoxy-beta-L-ribofuranosyl)-5-fluorocytosine in combination with a pharmaceutically acceptable additive, carrier or excipient.

3. A method of treating an HBV infection in a patient comprising administering to said patient a therapeutically effective amount of the compound 1-(2,3-Dideoxy-beta-L-ribofuranosyl)-5-fluorocytosine.

* * * * *